(12) United States Patent
Aquin et al.

(10) Patent No.: US 7,786,355 B2
(45) Date of Patent: Aug. 31, 2010

(54) PRODUCTION OF MEDIUM CHAIN LENGTH POLYHYDROXYALKANOATES FROM FATTY ACID BIOSYNTHETIC PATHWAYS

(75) Inventors: Stephanie Aquin, Montreal (CA); Oliver P. Peoples, Arlington, MA (US); Kristi D. Snell, Belmont, MA (US)

(73) Assignee: Metabolix, Inc., Cambridge, MA (US)

( * ) Notice: Subject to any disclaimer, the term of this patent is extended or adjusted under 35 U.S.C. 154(b) by 2018 days.

(21) Appl. No.: 09/991,152

(22) Filed: Nov. 16, 2001

(65) Prior Publication Data

US 2003/0017576 A1 Jan. 23, 2003

Related U.S. Application Data

(60) Provisional application No. 60/249,535, filed on Nov. 17, 2000.

(51) Int. Cl.
*A01H 5/00* (2006.01)
*C12N 15/82* (2006.01)
*C12N 1/20* (2006.01)
*C12N 5/10* (2006.01)

(52) U.S. Cl. .................. 800/298; 800/281; 435/419; 435/252.3

(58) Field of Classification Search ............. 800/281, 800/298
See application file for complete search history.

(56) References Cited

U.S. PATENT DOCUMENTS

| | | | |
|---|---|---|---|
| 5,034,322 A | 7/1991 | Rogers | |
| 5,245,023 A | 9/1993 | Peoples et al. | |
| 5,250,430 A | 10/1993 | Peoples et al. | |
| 5,268,463 A | 12/1993 | Jefferson | |
| 5,276,268 A | 1/1994 | Strauch et al. | |
| 5,364,780 A | 11/1994 | Hershey et al. | |
| 5,420,034 A | 5/1995 | Kridl et al. | |
| 5,464,765 A | 11/1995 | Coffee et al. | |
| 5,530,196 A | 6/1996 | Fraley et al. | |
| 5,591,616 A | 1/1997 | Hiei et al. | |
| 5,608,152 A | 3/1997 | Kridl et al. | |
| 5,650,554 A | 7/1997 | Moloney | |
| 5,668,298 A | 9/1997 | Waldron et al. | |
| 5,750,848 A * | 5/1998 | Kruger et al. ............... | 800/281 |
| 5,767,378 A | 6/1998 | Bojsen et al. | |
| 5,777,200 A | 7/1998 | Ryals et al. | |
| 5,846,767 A | 12/1998 | Halpin et al. | |
| 6,011,144 A | 1/2000 | Steinbuchel et al. | |
| 6,143,952 A | 11/2000 | Srienc et al. | |
| 6,329,183 B1 | 12/2001 | Skraly et al. | |
| 6,576,450 B2 | 6/2003 | Skraly et al. | |
| 2003/0211131 A1 | 11/2003 | Martin et al. | |
| 2004/0023347 A1 | 2/2004 | Skraly et al. | |
| 2005/0239179 A1 | 10/2005 | Skraly et al. | |

FOREIGN PATENT DOCUMENTS

| | | |
|---|---|---|
| EP | 0 530 129 A1 | 3/1993 |
| WO | WO 91/00917 A1 | 1/1991 |
| WO | WO 93/20216 | 10/1993 |
| WO | WO 98/06854 A1 | 2/1998 |
| WO | WO 98/54342 A1 | 12/1998 |
| WO | WO 00/08198 | 2/2000 |
| WO | WO 00/55328 | 9/2000 |
| WO | WO 2004/038030 | 5/2004 |

OTHER PUBLICATIONS

Broun et al, Science 282:1315-1317, Nov. 13, 1998.*
Van de Loo et al, PNAS, USA 92: 6743-6747, Jul. 1995.*
Doerks et al, TIG 14(6): 248-250, Jun. 1998.*
Smith et al, Nature Biotechnology 15: 1222-1223, Nov. 15, 1997.*
Brenner et al, S.E., TIG 15(4): 132-133, Apr. 1999.*
Bork et al, TIG 12(10): 425-427, Oct. 1996.*
DeLuca, V., AgBiotech News and Information 5(6): 225N-229N, 1993.*
Bevan, et al., "Structure and transcription of the nopaline synthase gene region of T-DNA," *Nucleic Acids Res.* 11:369-85 (1983).
Black, et al., "Cloning, sequencing, and expression of the *fadD* gene of *E. coli* encoding acyl coenzyme A synthetase," *J. Biol. Chem.* 267:25513-25520 (1992).
Clough & Bent, "Floral di[: a simplified method for Agrobacteriaum-mediated transformation of *Arabidopsis thaliana*," *Plant Journal* 16:735-743 (1998).
Cubitt, et al., "Understanding, improving and using green fluorescent proteins," *Trends Biochem. Sci.* 20(11):448-55 (1995).
Dasgupta, et al., "Co-ordinated expression of multiple enzymes in different subcellular compartments in plants," *The Plant Journal* 16:107-16 (1998)).
Fiedler, et al., "PhaG-mediated synthesis of poly(3-hydroxyalkanoates) consisting of medium-chain-length consituents from nonrelated carbon sources recombinant *Pseudonmona fragi*," *Applied and Environmental Microbiology* 66:2117-2124 (2000).

(Continued)

*Primary Examiner*—Elizabeth F McElwain
(74) *Attorney, Agent, or Firm*—Pabst Patent Group LLP

(57) ABSTRACT

Methods for producing polyhydroxyalkanoates (PHAs) from fatty acid biosynthetic pathways using a 3-hydroxy acyl ACP thioesterase, a PHA synthase, and an acyl CoA synthetase, have been developed. Methodology for enabling PHA production from fatty acid biosynthetic pathways in non-native bacterial PHA producers and plants using an enzyme having the catalytic activity of 3-hydroxy acyl ACP thioesterase, an acyl CoA synthetase with substrate specificity for medium chain length 3-hydroxy fatty acids, and a medium chain length PHA synthase, has been developed. Acyl CoA synthetase activity can be supplied either by the endogenous acyl CoA synthetase of the host organism, when sufficiently expressed, or the host organism's activity can be supplemented by the expression of a recombinant acyl CoA synthetase gene. New strategies are described for plant based PHA production in the chloroplasts, cytosol, and peroxisomes of biomass crops as well as the plastids, cytosol, and peroxisomes of oil seed crops.

22 Claims, 5 Drawing Sheets

OTHER PUBLICATIONS

Fromm, et al., "Inheritance and expression of chimeric genes in the progeny of transgenic maize plants," *Biotechnology* (NY). 8(9):833-39 (1990).

Gasser & Fraley, "Genetically Engineering Plants for Crop Improvement," *Science* 244:1293-1299 (1989).

Hoffmann. "The *Pseudomonas aeruginosa* phaG gene product is involved in the synthesis of polyhydroxyalkanoic acid consisting of medium-chain-length constituents from non-related carbon sources," *FEMS Microbiology Letters* 184:253-259 (2000).

Hood et al, "The hypervirulence of *Agrobacterium tumefaciens* A281 is encoded in a region of pTiBo542 outside of T-DNA," *J. Bacteriol.* 168:1291-301 (1986).

Huisman, et al., "Metabolism of poly(3-hydroxyalkanoates) (PHAs) by *Pseudomonas oleovorans*. Identification and sequences of genes and function of the encoded proteins in the synthesis and degradation of PHA," *J. Biol. Chem.* 266(4):2191-08 (1991).

Jefferson, et al., "GUS fusions: β-glucuronidase as a sensitive and versatile gene fusion marker in higher plants," *EMBO J.* 6(13):3901-07 (1987).

Kato, et al., "Production of a novel copolyester of 3-hydroxybutyric acid with a medium-chain-length 3-hydroxyalkanoic acids by *Pseudomonas* sp. 61-3 from sugars," *Appl. Microbiol. Blotechnol.* 45:363-70 (1996).

Khoudi, et al., "An alfalfa rubisco small subunit homologue shares *cis*-acting elements with the regulatory sequences of the RbcS-3A gene from pea," *Gene* 197:343-51 (1997).

Klinke, et al., "Production of medium-chain-length poly(3-hydroxyalkanoates) from gluconate by recombinant *Escherichia coli*," *Appl. Environ. Microbiol.* 65:540-548 (1999).

Kyozuka, et al., "Anaerobic induction and tissue-specific expression of maize *Adh1* promoter in transgenic rice plants and their progeny," *Mol. Gen. Genet.* 228(1-2):40-48 (1991).

Lee, et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33," *Appl. Microbiol. Biotechnol.* 42: 901-909 (1995).

Madison & Huisman, "Metabolic engineering of Poly(3-Hydroxyalkanoates): From DNA to Plastic," *Microbiology and Molecular Biology Reviews* 63:21-53 (1999).

Maliga, et al., *Methods in Plant Molecular Biology: A Laboratory Course Manual*, Cold Spring Laboratory Press:New York, 1995.

Martinez, et al., "pACYC184-derived cloning vectors containing the multiple cloning site and lacZα reporter gene of pUC8/9 and pUC18/19 plasmids," *Gene* 68:159 (1988).

Matesanz, et al., "The cloning and expression of Pfacs1, a *Plasmodium falciparum* fatty acyl coenzyme A synthase-1 targeted to the host erythrocyte cytoplasm," *J. Mol. Biol.* 291:59-70 (1999).

McElroy, et al., "Isolation of an efficient actin promoter for use in rice transformation," *Plant Cell.* 2(2):163-71 (1990).

Moloney, et al., "High efficiency transformation of *Brassica napus* using *Agrobacterium* vectors," *Plant Cell Reports* 8:238-42 (1989).

Nawrath, et al., "Review of Polyhydroxyalkanoate formation in the model plant *Arabidopsis thaliana*," *PNAS* 91:12760-12764 (1994).

Ochsner, et al., "Isolation, characterization, and expression in *Escherichia coli* of the *Pseudomonas aeruginosa* rhLaB genes encoding a rhamnosyltransferase involved in rhamnolipid biosurfactant synthesis," *J. Biol. Chem.* 269:19787-19795 (1994).

Odell, et al., "Identification of DNA sequences required for activity of the cauliflower mosaic virus 35S promoter," *Nature* 313(6005):810-12 (1985).

Olsen, et al., *Plant Cell* 5:941-952 (1993).

Owen & Pen, eds., *Transgenic Plants: A Production System for Industrial and Pharmaceutical Proteins* John Wiley & Sons Ltd: England, 1996.

Pang, et al., "An Improved green fluorescent protein gene as a vital marker in plants," *Plant Physiol.* 112:893-900 (1996).

Plant, et al., "Regulation of an *Arabidopsis oleosin* gene promoter in transgenic *Brassica napus*," *Plant Mol. Biol.* 25(2):193-205 (1994).

Potrykus & Spangenberg, *Gene Transfer to Plants*, Springer-Verlag:Berlin Heidelberg New York, 1995.

Rehm, et al., "A new metabolic link between fatty acid *de Novo* synthesis and polyhydroxyalkanoic acid synthesis," *J. Biol. Chem.* 273:24044-51 (1998).

Reusch, "Low molecular weight complexed [poly(3-hydroxybutyrate): a dynamic and versatile molecule in vivo," *J. Microbiol.* 41(suppl. 1):50-54 (1995).

Rowley & Herman, "The upstream domain of soybean oleosin genes contains regulatory elements similar to those of legume storage proteins," *Biochim. Biophys. Acta.* 1345(1):1-4 (1997).

Sheen, "Protein phosphatase activity is required for light-inducible gene expression in maize," *J. EMBO* 12:3497-505 (1993).

Slightom, et al., *Proc. Natl. Acad. Sci.* 80 USA:1897-901 (1983).

Söhling & Gottschalk, "Molecular analysis of the anaerobic succinate degradation pathway in *Clostridium kluyveri*," *J. Bacteriol.* 178:871-880 (1996).

Steinbüchel and Valentin, "Diversity of bacterial polyhydroxyalkanoic acids," *FEMS Microbiol. Lett.* 128:219-28 (1995).

Timm & Steinbüchel, "Cloning and molecular analysis of the poly(3-hydroxyalkanoic acid) gene locus of *Pseudomonas aeruginosa* PAO1," *Eur. J. Biochem.* 209(1):15-30 (1992).

Van Beilen, et al., "DNA sequence determination and functional characterization of the OCT-plasmid-encoded *alkJKL* genes of *Pseudomonas oleovorans*," *Mol. Microbiol.* 6: 3121-36 (1992).

Vogel & Bonner, "Acetylornithinase of *Escherichia coli*: Partial purification and some properties," *J. Biol. Chem.* 218:97-106 (1956).

Williams & Peoples, "Biodegradable plastics from plants," CHEMTECH 26:38-44 (1996).

Garcia, et al., "Novel biodegradable aromatic plastics from a bacterial source. Genetic and biochemical studies on a route of the phenylacetyl-coa catabolon", *J. Biol. Chem.*, 274(41):29228-41 (1999).

Ohlrogge, et al., "Alteration of acyl-acyl carrier protein pools and acetyl-CoA carboxylase expression in *Escherichia coli* by a plant medium chain acyl-acyl carrier protein thioesterase", *Arch. Biochem. Biophys.*, 317(1):185-90 (1995).

Poirier, et al., "Increased flow of fatty acids toward beta-oxidation in developing seeds of *Arabidopsis* deficient in diacylglycerol acyltransferase activity or synthesizing medium-chain-length fatty acids", *Plant Physiol.*, 121(4):1359-66 (1999).

Williams, et al., "PHA applications: addressing the price performance issue: I. Tissue engineering", *Int. J. Biol. Macromol.*, 25(1-3):111-21 (1999).

* cited by examiner

FIG. 1
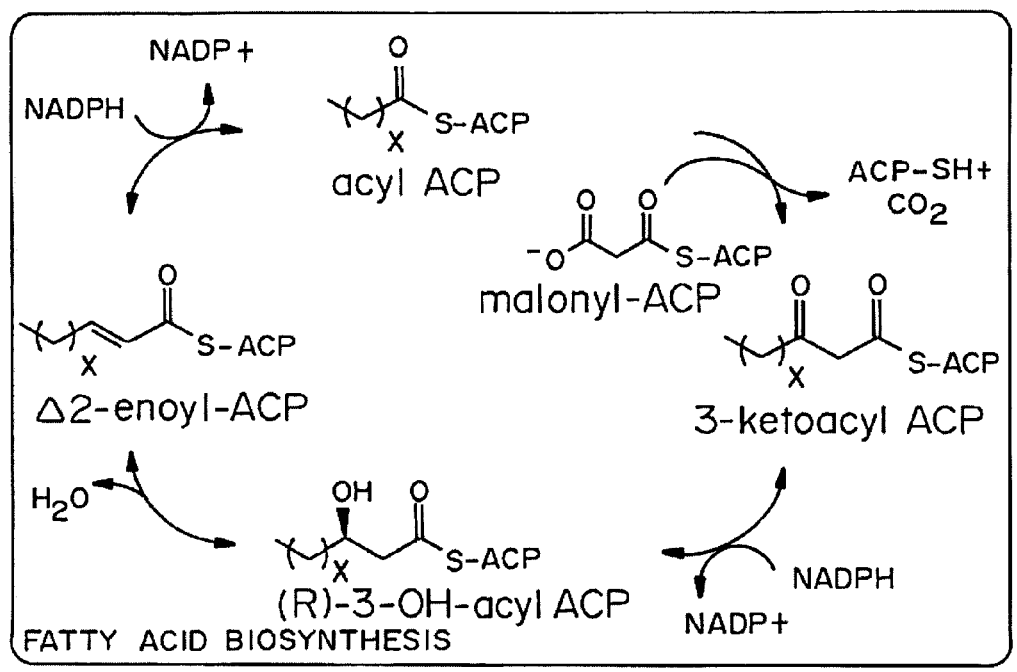
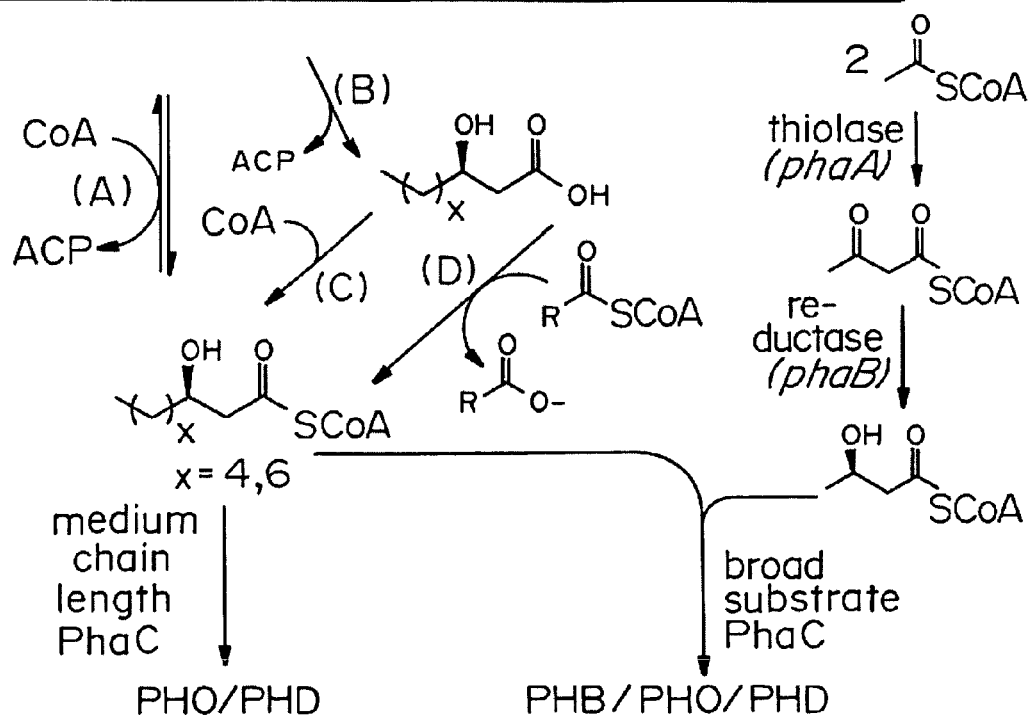

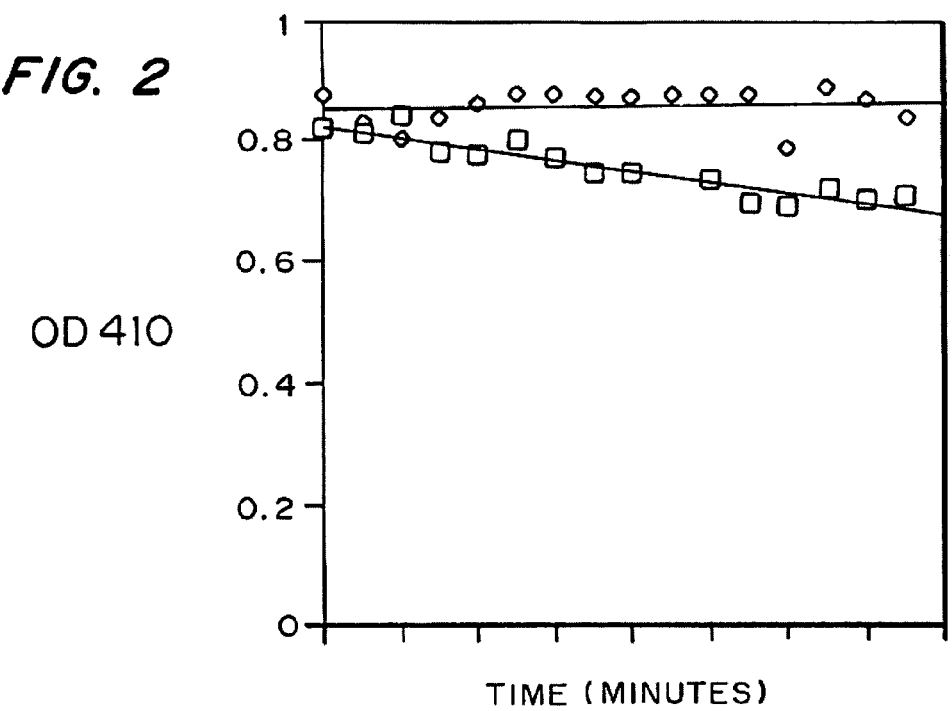
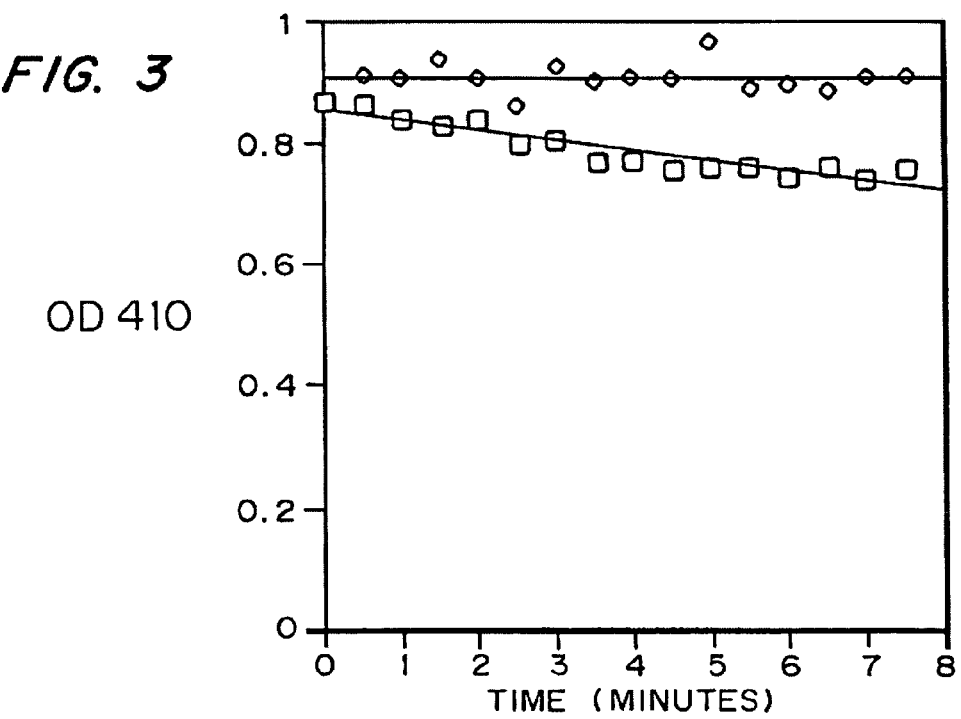

pCambia-Rbc.PhaG.PhaC pBI-C4PPDK.PhaG.Rbc.PhaC

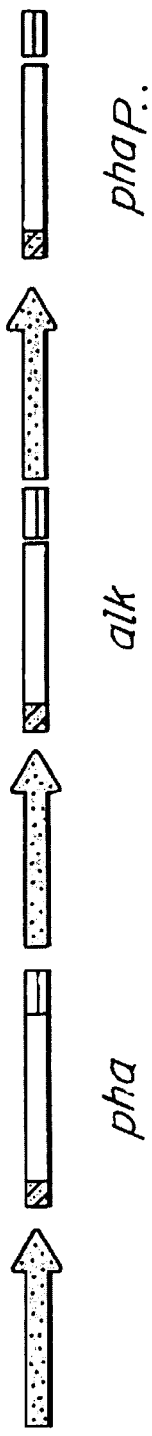
FIG. 5A Chloroplast PHA Production
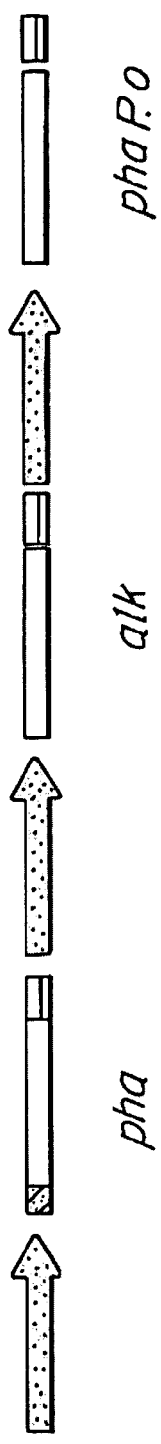
FIG. 5B Cytosolic PHA Production
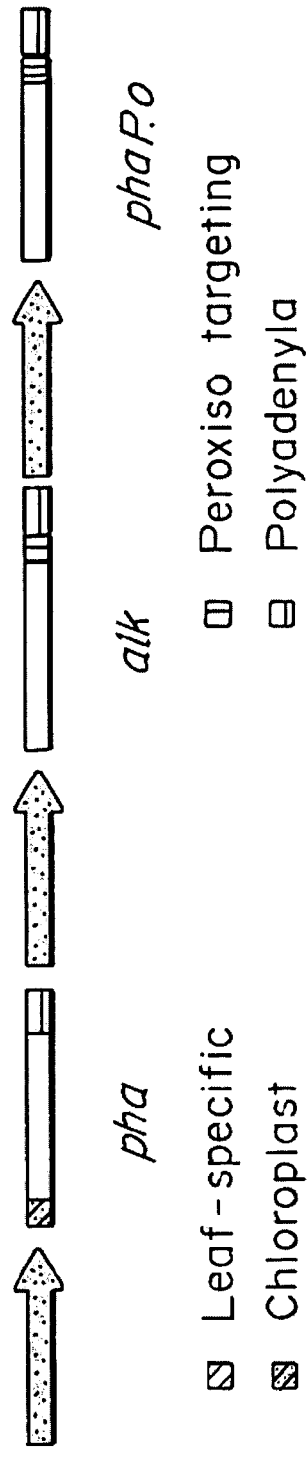
FIG. 5C Peroxisomal Production Plastid PHA Production Cytosolic PHA Production Peroxisomal Production

PRODUCTION OF MEDIUM CHAIN LENGTH POLYHYDROXYALKANOATES FROM FATTY ACID BIOSYNTHETIC PATHWAYS

CROSS REFERENCE TO RELATED APPLICATIONS

Priority is claimed to U.S. Provisional application Ser. No. 60/249,535, filed Nov. 17, 2000, the teachings of which are incorporated herein.

BACKGROUND OF THE INVENTION

Numerous microorganisms have the ability to accumulate intracellular reserves of Poly [(R)-3-hydroxyalkanoates] (PHAs). PHAs are biodegradable and biocompatible thermoplastic materials, produced from renewable resources, with a broad range of industrial and biomedical applications (Williams and Peoples, 1996, CHEMTECH 26, 38-44). The PHA biopolymers encompass a broad class of polyesters with different monomer compositions and a wide range of physical properties. To date around 100 different monomers have been incorporated into the PHA polymers (Steinbüchel and Valentin, 1995, FEMS Microbiol. Lett. 128; 219-228). PHAs can be divided into two groups according to the length of their side chains. Those with short side chains, such as polyhydroxybutyrate (PHB), a homopolymer of R-3-hydroxybutyric acid units, are crystalline thermoplastics, whereas PHAs with medium length side chains, such as polyhydroxyoctanoic or polyhydroxydecanoic acid, are more elastomeric.

In bacteria, each PHA group is produced by a specific pathway. In the case of the short pendant group PHAs, three enzymes are involved, a β-ketothiolase, an acetoacetyl-CoA reductase, and a PHA synthase. For example, in PHB biosynthesis two molecules of acetyl-coenzyme A are condensed by a β-ketothiolase to yield acetoacetyl-coenzyme A. The latter is then reduced to the chiral intermediate R-3-hydroxybutyryl-coenzyme A by the reductase, and subsequently polymerized by the PHA synthase enzyme. Short chain length PHA synthases typically allow polymerization of C3-C5 hydroxy acid monomers including both 4-hydroxy and 5-hydroxy acid units. This biosynthetic pathway is found in a number of bacteria such as *Ralstonia eutropha, Alcaligenes latus, Zoogloea ramigera*, etc (Madison, L. L. & Huisman, G. W. Microbiology and Molecular Biology Reviews 1999, 63, 21-53).

Medium chain length pendant group PHAs are produced by many different *Pseudomonas* bacteria. The hydroxyacyl-coenzyme A monomeric units can originate from fatty acid β-oxidation and fatty acid biosynthetic pathways. The monomer units are then converted to polymer by PHA synthases which have substrate specificity's favoring the larger C6-C14 monomeric units (Madison, L. L. & Huisman, G. W. Microbiology and Molecular Biology Reviews 1999, 63, 21-53). In the *Pseudomonas* organisms, the PHA synthases responsible for production of the long pendant group PHAs were found to be encoded on the pha locus, specifically by the phaA and phaC genes (U.S. Pat. Nos. 5,245,023; 5,250,430; Huisman et. al., 1991, J. Biol. Chem. 266:2191-2198).

Co-polymers comprised of both short and medium chain length pendant groups can also be produced in bacteria possessing a PHA synthase with a broad substrate specificity. For example, *Pseudomonas* sp. A33 (Appl. Microbiol. Biotechnol. 1995, 42, 901-909), *Pseudomonas* sp. 61-3 (Kato, M., Bao, H. J., Kang, C. -K, Fukui, T., Doi, Y. Appl. Microbiol. Biotechnol. 1996, 45, 363-370), and *Thiocapsa pfennigii* (U.S. Pat. No. 6,011,144) all possess PHA synthases that have been reported to produce co-polymers of short and medium chain length monomer units.

An enzyme encoded by phaG was recently identified in both *Pseudomonas putida* and *Pseudomonas aeruginosa* and has been reported to be the link between fatty acid biosynthesis and medium chain length PHA formation (see Pathway A in FIG. 1) in these organisms (Rehm, B. H. A., Kruger, N., Steinbuchel, A. J. Biol. Chem. 1998, 273, 24044-24051; WO 98/06854; U.S. Pat. No. 5,750,848; Hoffmann, N., Steinbuchel, A., Rehm, B. H. A. FEMS Microbiology Letters, 2000, 184, 253-259). In these studies, PhaG was identified as a 3-hydroxyacyl-acyl carrier protein-coenzyme A transferase based on the ability of partially purified enzyme preparations to convert 3-hydroxydecanoyl CoA in the presence of ACP to 3-hydroxydecanoyl ACP (Rehm, B. H. A., Kruger, N., Steinbuchel, A. J. Biol. Chem. 1998, 273, 24044-24051). Expression of PhaG and PhaC in *Pseudomonas fragi*, an organism that does not naturally produce PHAs as a storage material, enabled the production of PHAs from gluconate (Fiedler, S., Steinbuchel, A., Rehm, B. H. A. Applied and Environmental Microbiology 2000, 66, 2117-2124). No polymer however was observed upon expression of a medium chain length synthase and PhaG in *E. coli* (Rehm, B. H. A., Kruger, N., Steinbuchel, A. J. Biol. Chem. 1998, 273, 24044-24051). While *E. coli* is capable of producing small amounts of low molecular weight, non-granule forms of PHB (Reusch, R. N. Can. J. Microbiol. 1995, 41 (suppl. 1), 50-54), like *P. fragi*, it is unable to produce granules of storage polymer.

U.S. Pat. No. 5,750,848 reported that the phaG gene from *Pseudomonas putida* encodes a 3-hydroxyacyl-ACP—CoA transferase activity useful for producing (D)-3-hydroxyacyl-CoA precursors for the biosynthesis of polyhydroxyalkanoate (PHA) biopolymers comprising C8 and C10 units. This activity has not been confirmed, however.

It is therefore an object of the present invention to express PhaG in conjunction with an acyl CoA synthetase and a PHA synthase in an organism for the production of PHAs.

It is therefore further object of the present invention to express PhaG in conjunction with an acyl CoA synthetase and a PHA synthase in an organism for the production of medium chain length PHAs.

SUMMARY OF THE INVENTION

It has been discovered that a recombinant *E. coli* system expressing the phaG gene and PHA synthase 1 gene from *Pseudomonas oleovorans* does not accumulate medium chain length PHAs. However, it was found that the media contained significant levels of 3-hydroxyacids. It has now been shown that the PhaG protein was functioning as a 3-hydroxyacyl-ACP thioesterase. An *E. coli* system expressing the phaG gene, the phaC1 gene and the alkK gene produces PHA. These results not only provide new metabolic engineering approaches to produce PHAs in *E. coli* or other bacteria but provide several new approaches for producing PHAs in other organisms, for example, plant crops.

The methods described herein include expressing enzymes having 3-hydroxyacyl-ACP thioesterase activity in the plastids of leaves or seeds of plant crops or in an organism other than a plant such as bacteria in conjunction with, for example, an acyl CoA synthetase or CoA transferase, or a PHA synthase gene or genes, in the case of a two-subunit synthase, in the peroxisome, cytosol or plastids of higher plants. In some cases such as plastid expression of the thioesterase and PHA synthase, it is also useful to express a gene having a 3-hydroxyacyl-CoA synthetase activity in the plastid. Where the PHA synthase is expressed in the cytosol, it may optionally be useful to increase the expression of a gene or genes encoding an enzyme having the catalytic activity of a (D)-3-hydroxyacyl-CoA synthetase. Where the PHA synthase is targeted to the peroxisome, it may also be useful to also target an enzyme having the catalytic activity of a (D)-3-hydroxyacyl-CoA synthetase to the peroxisome.

A transgene construct that encodes an enzyme having the catalytic activity of a 3-hydroxyacyl-ACP thioesterase has been developed. In one embodiment, the transgene construct further includes a gene encoding an acyl CoA synthetase or a CoA transferase. In another embodiment, the transgene construct further includes a gene encoding an acyl CoA synthetase or a CoA transferase and a gene encoding a PHA synthase.

The transgene construct can be expressed in any organism and/or cells thereof for the production of PHAs. In one example, the PHA is a medium chain length PHA having, for example, C8 and C10 hydroxyacid units. In another example, the organism is bacteria. In another example, the organism is a plant. PHAs can be produced by growing the organism or cells thereof under appropriate conditions.

The method described herein also allows for the modification of the plant oil composition to increase the levels of C8 and C10 hydroxyacids or fatty acids.

BRIEF DESCRIPTION OF THE DRAWINGS

FIG. 1 is the proposed pathways for medium chain length polyhydroxyalkanoate and short and medium chain length polyhydroxyalkanoate co-polymer formation from fatty acid biosynthesis.

FIG. 2 is a graph indicating the consumption of CoA with time in the presence of octanoic acid in crude extracts prepared from strains DH5α/pTRCNalkK and DH5α/pTRCN.

FIG. 3 is a graph indicating the consumption of CoA with time in the presence of 3-hydroxyoctanoic acid in crude extracts prepared from strains DH5α/TRCNalkK and DH5α/pTRCN.

FIG. 5A is the map of inserts in the plant transformation vector for leaf-specific expression of phaG, alkK and phaC for the accumulation of polymer in the chloroplasts of leaves.

FIG. 5B is the map of inserts in the plant transformation vector for leaf-specific expression of phaG, alkK and phaC for the accumulation of polymer in the cytosol of leaves.

FIG. 5C is the map of inserts in the plant transformation vector for leaf-specific expression of phaG, alkK and phaC for the accumulation of polymer in the peroxisomes of leaves.

DETAILED DESCRIPTION OF INVENTION

Figure 4A:
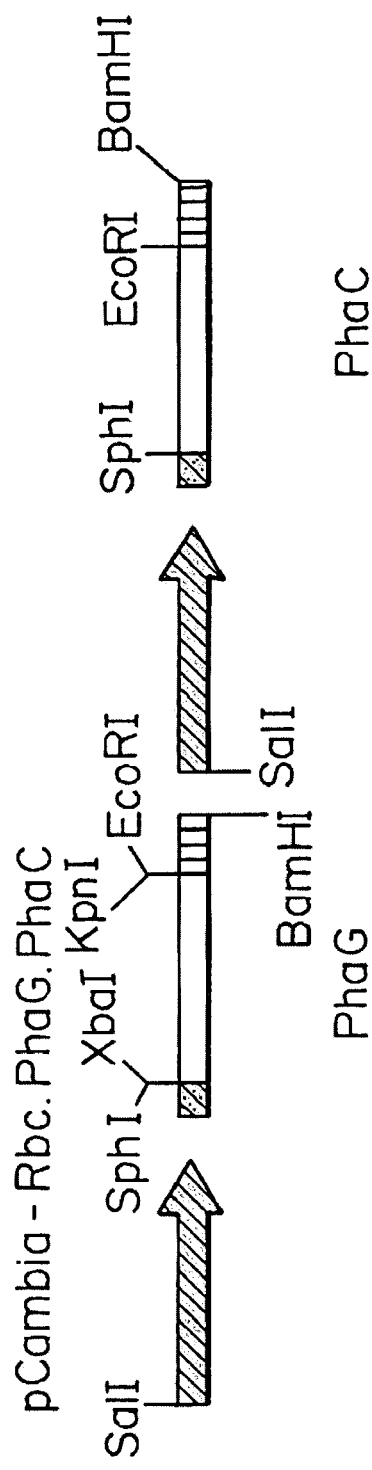
FIG. 4A shows the map of insert in pCambia-Rbc.PhaG-.PhaC containing the alfalfa rubisco promoter fused to the alfalfa chloroplast targeting signal, a fragment encoding PhaG, a fragment encoding the alfalfa rubisco termination sequence, the alfalfa rubisco promoter fused to the alfalfa chloroplast targeting signal, a fragment encoding PhaC from *Pseudomonas aeroginosa*, and a fragment encoding the alfalfa rubisco termination sequence.

The inability of *E. coli* to form medium chain length PHAs from glucose when expressing PhaG and PhaC suggests that an additional enzyme activity may be required when this pathway is engineered into non-native PHA producers that are not Pseudomonads. U.S. Pat. No. 5,750,848 describes screening methods to isolate an enzyme or combination of enzymes that allow conversion of 3-hydroxy acyl ACPs to 3-hydroxy acyl CoAs in PHA negative bacteria, but such enzymes are not described in the patent. Klinke et al. (Klinke, S., Ren, Q., Witholt, B., Kessler, B. Appl. Environ. Microbiol. 1999, 65, 540-548) have demonstrated PHA production in *E. coli* upon coexpression of a thioesterase and a PHA synthase. Since the thioesterase employed by Klinke et al. does not convert 3-hydroxy acyl ACPs to 3-hydroxy fatty acids but instead converts acyl ACPs to fatty acids, the host cell's native β-oxidation enzymes are required to form the 3-hydroxy acyl CoAs for PHA formation. This strategy is therefore limited in plants since β-oxidation enzymes are localized predominantly in the peroxisomes limiting the location that PHA can be produced.

An acyl CoA synthetase as an enzyme activity which is required for medium chain length PHA production in heterologous systems expressing PhaG and PhaC has been discovered. Acyl CoA synthetases catalyze the conversion of free fatty acids, coenzyme A, and ATP to fatty acyl CoAs plus AMP (see Pathway C in FIG. 1; Black, P. N., DiRusso, C. C., Metzger, A. K., Heimert, T. L. J. Biol. Chem. 1992, 267, 25513-25520). The requirement of supplemental acyl CoA synthetase activity to enable PhaG to complete the 3-hydroxy acyl ACP-CoA transferase reaction in vivo suggests that PhaG unexpectedly encodes only 3-hydroxy acyl ACP thioesterase activity (see Pathway B in FIG. 1). Genes for acyl CoA synthetases have been isolated and characterized, including the fadD gene from *E. coli* (Black, P. N., DiRusso, C. C., Metzger, A. K., Heimert, T. L. J. Biol. Chem. 1992, 267, 25513-25520), the alkK gene from *Pseudomonas oleovorans* (van Beilen, J. B., Eggink, G., Enequist, H., Bos, R., Witholt, B. Molecular Microbiology 1992, 6, 3121-3136), and the Pfacs1 gene from *Plasmodium falciparum* (Matesanz, F., Duran-Chica, I., Alcina, A. J. Mol. Biol. 1999, 291, 59-70).

Like acyl CoA synthetases, CoA transferases are also able to convert 3-hydroxy fatty acids to 3-hydroxy acyl CoAs. CoA transferases catalyze the transfer of CoA from an acyl CoA to a free fatty acid (see Pathway D in FIG. 1). Coexpression of a 3-hydroxy acyl ACP thioesterase with a CoA transferase should allow the successful conversion of a 3-hydroxyacyl ACP to its corresponding 3-hydroxy acyl CoA. WO 98 39453 describes methods for utilizing CoA transferase and PHA synthase activities to produce short chain length PHAs in host organisms but does not describe the combined use of 3-hydroxy acyl ACP thioesterases and CoA transferases to convert 3-hydroxy acyl ACP to 3-hydroxy acyl CoA. To obtain a CoA transferase capable of transferring CoA from a readily available CoA thioester in the host organism to a medium chain length fatty acid, genomic DNA libraries can be constructed and screened in PHA minus bacteria expressing a suitable medium chain length PHA synthase and a 3-hydroxy acyl ACP thioesterase. Alternatively, gene shuffling of existing CoA transferases, such as the orfZ gene from *Clostridium kluyveri* (Sohling, B. & Gottschalk, G. J. Bacteriol. 1996, 178, 871-880), can be used to create new CoA transferases with the ability to transfer CoA from a readily available CoA thioester in the host organism to a medium chain length fatty acid. New CoA transferases containing the desired activity can be screened in PHA minus bacteria expressing a suitable medium chain length PHA synthase and a 3-hydroxy acyl ACP thioesterase.

Methodology for engineering plants to produce PHAs comprising medium chain length (D)-3-hydroxyacids from fatty acid biosynthetic pathways by expressing an enzyme having the catalytic activity of 3-hydroxyacyl ACP thioesterase, a PHA synthase capable of incorporating medium chain 3-hydroxyacids, and an enzyme having either (D)-3-hydroxyacyl-CoA synthetase activity or CoA transferase activity, has been developed. The methodology described herein is useful for engineering both oil seed and biomass crops to produce the desired PHA biopolymers.

Methods and materials for identification of acyl CoA synthetase as an enzyme activity whose presence is required for polymer production from fatty acid biosynthetic pathways in recombinant *E. coli* expressing phaG and a medium chain length PHA synthase (PhaC) are also described herein. Specifically, it is demonstrated that co-expression of PhaG, an enzyme previously characterized as a 3-hydroxyacyl-ACP—CoA transferase (U.S. Pat. No. 5,750,848), and PhaC in *E. coli* and *Arabidopsis thaliana* yields no intracellular inclusions of polymer. In the bacterial system, an excretion of 3-hydroxyacids into the culture supernatant is observed indicating that a PhaG catalyzed diversion of carbon from fatty acid biosynthesis is occurring. Co-expression of alkK, an acyl CoA synthetase from *P. oleovorans* that possesses activity on medium chain length 3-hydroxy fatty acids, results in the intracellular accumulation of medium chain length polymer and a reduction in the amount of 3-hydroxy acids excreted into the culture medium. The ability of *E. coli* cells expressing phaC and phaG to produce polymer only upon expression of alkK suggests that PhaG is behaving as a 3-hydroxy acyl ACP thioesterase, not an acyl ACP-CoA transferase in vivo in *E. coli*. Plants expressing phaG and phaC may also require supplemental acyl CoA synthetase activity for successful PHA production from fatty acid biosynthetic pathways.

PHA synthases are known in the art and can also be developed from other PHA synthases by known techniques as described for example in U.S. Pat. No. 6,143,952.

DNA constructs described herein include transformation vectors capable of introducing transgenes into plants. There are many plant transformation vector options available (Gene Transfer to Plants (1995), Potrykus, I. and Spangenberg, G. eds. Springer-Verlag Berlin Heidelberg New York; "Transgenic Plants: A Production System for Industrial and Pharmaceutical Proteins" (1996), Owen, M. R. L. and Pen, J. eds. John Wiley & Sons Ltd. England and Methods in Plant Molecular Biology—a laboratory course manual (1995), Maliga, P., Klessig, D. F., Cashmore, A. R., Gruissem, W. and Varner, J. E. eds. Cold Spring Laboratory Press, New York) which are incorporated herein by reference. In general, plant transformation vectors comprise one or more coding sequences of interest under the transcriptional control of 5' and 3' regulatory sequences, including a promoter, a transcription termination and/or polyadenylation signal and a selectable or screenable marker gene. The usual requirements for 5' regulatory sequences include a promoter, a transcription initiation site, and a RNA processing signal. 3' regulatory sequences include a transcription termination and/or a polyadenylation signal.

A large number of plant promoters are known and result in either constitutive, or environmentally or developmentally regulated expression of the gene of interest. Plant promoters can be selected to control the expression of the transgene in different plant tissues or organelles for all of which methods are known to those skilled in the art (Gasser and Fraley, 1989, Science 244; 1293-1299). Suitable constitutive plant promoters include the cauliflower mosaic virus 35S promoter (CaMV) and enhanced CaMV promoters (Odell et. al., 1985, Nature, 313: 810), actin promoter (McElroy et al., 1990, Plant Cell 2: 163-171), AdhI promoter (Fromm et. al., 1990, Bio/Technology 8: 833-839; Kyozuka et al., 1991, Mol. Gen. Genet. 228: 40-48), ubiquitin promoters, the Figwort mosaic virus promoter, mannopine synthase promoter, nopaline synthase promoter and octopine synthase promoter. Useful regulatable promoter systems include spinach nitrate-inducible promoter, heat shock promoters, small subunit of ribulose biphosphate carboxylase promoters and chemically inducible promoters (U.S. Pat. Nos. 5,364,780; 5,364,780; 5,777,200).

In one embodiment, an enzyme having the catalytic activity of 3-hydroxy acyl ACP thioesterase and an acyl CoA synthetase are utilized to convert 3-hydroxy acyl ACPs to 3-hydroxy acyl CoAs. Coexpression of a PHA synthase allows PHA formation. In one embodiment, the host organism's endogenous acyl CoA synthetase activity, if present in sufficient amounts, is utilized. In an alternative embodiment, the acyl CoA synthetase activity of the host organism is supplemented by overexpression of a gene encoding acyl CoA synthetase, such as the alkK gene from *Pseudomonas oleovorans* (van Beilen, J. B., Eggink, G., Enequist, H., Bos, R., Witholt, B. Molecular Microbiology 1992, 6, 3121-3136).

In another embodiment, an enzyme having the catalytic activity of 3-hydroxy acyl ACP thioesterase and an enzyme encoding acyl CoA transferase activity are utilized. In this embodiment, the acyl CoA transferase catalyzes the transfer of CoA from an acyl CoA readily available in the host organism to the 3-hydroxy fatty acid resulting in 3-hydroxy acyl CoA formation. Coexpression of a PHA synthase allows PHA formation.

In one embodiment, genes encoding enzymes with activities related to 3-hydroxy acyl ACP thioesterases, or genes encoding enzymes with some homology to PhaG, are modified by molecular evolution or gene shuffling techniques to yield novel enzymes with medium chain length 3-hydroxy acyl ACP thioesterase activities. U.S. Pat. No. 5,750,848 describes producing variants of PhaG but does not describe modifying related enzymes to produce novel 3-hydroxy acyl ACP thioesterase activity. In one embodiment of this aspect of the invention, the rhlAB genes from *Pseudomonas aeruginosa*, encoding rhamnosyltransferase activity (Ochsner, U. A., Fiechter, A., Reiser, J. J. Biol. Chem. 1994, 269, 19787-19795), are modified by gene shuffling. Specifically, the rhlAB, rhlA, or rhlB coding regions, or segments of any of the aforementioned coding regions, are modified by gene shuffling to produce enzymes encoding medium chain length 3-hydroxy acyl ACP thioesterase activities. Libraries of shuffled genes can be tested for complementation of phaG mutant strains or in heterologous bacteria expressing a suitable PHA synthase and a 3-hydroxyacyl-CoA synthetase.

In one embodiment, transgenes are expressed only in the leaf. A suitable promoter for this purpose would include the C4PPDK promoter preceded by the 35S enhancer (Sheen, J. EMBO, 1993, 12, 3497-3505) or any other promoter that is useful for expression in the leaf. In one embodiment of leaf-specific transgene expression, the 5' end of the transgenes encoding an enzyme having the catalytic activity of 3-hydroxy acyl ACP thioesterase, PHA synthase, and acyl CoA synthetase activities are engineered to include sequences encoding chloroplast targeting peptides linked in-frame with the transgene. A chloroplast targeting sequence is any peptide sequence that can target a protein to the chloroplasts or plastids, such as the transit peptide of the small subunit of the alfalfa ribulose-biphosphate carboxylase (Khoudi, H., Vezina, L. -P., Mercier, J., Castonguay, Y., Allard, G., Laberge, S. Gene 1997, 197, 343-351) or the pea rubisco chloroplast targeting signal (Cashmore, A. R. (1983) in Genetic Engineering of plants, eds. Kosuge, T., Meredith, C. P. & Hollaender, A. (Plenum, New York), p 29-38; Nawrath, C., Poirier, Y. and Somerville, C. (1994) *PNAS.* 91: 12760-12764). The transport of all polypeptides to the chloroplast will result in polymer accumulation in the chloroplast. In one embodiment, a chloroplast targeted CoA transferase is utilized instead of an acyl CoA synthetase. In this embodiment, the CoA transferase catalyzes the transfer of CoA from an acyl CoA present in the host organism to the 3-hydroxy fatty acid forming the monomer unit for PHA synthase.

In another embodiment of leaf-specific transgene expression, only the phaG transgene is engineered to include a sequence encoding a chloroplast targeting peptide. A transgene encoding PhaC is not targeted to an organelle allowing transport of the polypeptide into the cytosol. In this embodiment, medium chain length 3-hydroxy fatty acids are diverted from fatty acid biosynthesis by PhaG and are predominantly exported from the chloroplast into the cytosol so that they can be incorporated into triacylglycerols or directed to the peroxisomes for degradation. The presence of cytosolic PhaC enables the conversion of a portion of the unusual fatty acids to PHAs prior to their degradation or incorporation into lipids. In one embodiment, the endogenous acyl CoA synthetase of the plant is supplemented by expression of a transgene encoding an acyl CoA synthetase directed to the cytosol. In an alternative embodiment of the invention, a CoA transferase is utilized instead of an acyl CoA synthetase.

In an alternative embodiment, transgenes are expressed only in developing seeds. Promoters suitable for this purpose include the napin gene promoter (U.S. Pat. Nos. 5,420,034; 5,608,152), the acetyl-CoA carboxylase promoter (U.S. Pat. Nos. 5,420,034; 5,608,152), 2S albumin promoter, seed storage protein promoter, phaseolin promoter (Slightom et. al., 1983, Proc. Natl. Acad. Sci. USA 80: 1897-1901), oleosin promoter (plant et. al., 1994, Plant Mol. Biol. 25: 193-205; Rowley et. al., 1997, Biochim. Biophys. Acta.1345: 1-4; U.S. Pat. No. 5,650,554; PCT WO 93/20216), zein promoter, glutelin promoter, starch synthase promoter, starch branching enzyme promoter etc.

In one embodiment of seed-specific transgene expression, the 5' end of transgenes encoding an enzyme having the catalytic activity of 3-hydroxy acyl ACP thioesterase, PHA synthase, and acyl CoA synthetase are engineered to include sequences encoding plastid targeting peptides linked in-frame with the transgene. A plastid targeting sequence is any peptide sequence that can target a protein to the chloroplasts or plastids. The direction of all polypeptides to the plastid will result in polymer accumulation predominantly in the plastid of the seed. In an alternative embodiment, a plastid targeted CoA transferase is utilized instead of an acyl CoA synthetase.

In another embodiment of seed-specific expression, only the phaG transgene is engineered to include a sequence encoding a plastid targeting peptide. A transgene encoding PhaC is not targeted to an organelle allowing transport of the polypeptide into the cytosol. In this embodiment, the 3-hydroxyacyl fatty acids diverted from fatty acid biosynthesis by PhaG are exported from the plastid and converted to PHAs in the cytosol of the developing seed by cytosolic PhaC. In one embodiment, the endogenous acyl CoA synthetase of the plant is supplemented by expression of a transgene encoding an acyl CoA synthetase directed to the cytosol. In an alternative embodiment, a CoA transferase is utilized instead of an acyl CoA synthetase.

In an alternative embodiment, PHA production can be targeted to leaf or seed peroxisomes. In this embodiment, the 5' end of the phaG transgene is engineered to include a sequence encoding a chloroplast or plastid targeting peptide linked in-frame with the transgene. The phaC transgene is linked in frame with a suitable N-terminal or C-terminal peroxisomal targeting sequence. A peroxisomal targeting signal is any peptide sequence that can target a protein to leaf or seed peroxisomes, such as the C-terminal 34 amino acids of the *Brassica napus* isocitrate lyase (Olsen, L. J., Ettinger, W. F., Damsz, B., Matsudaira, K., Webb, M. A., Harada, J. J. 1993, Plant Cell, 5, 941-952). 3-hydroxyacyl fatty acids diverted from chloroplast or plastid fatty acid biosynthesis by PhaG are exported from the organelle and are either transported into the peroxisomes for degradation or incorporated into triacylglycerides. The presence of peroxisomally targeted PhaC would convert 3-hydroxy fatty acids entering the peroxisomes into PHAs. Incorporation of medium chain length 3-hydroxy fatty acids into triacylglycerides in the seed would produce novel plant oils. In one embodiment, the endogenous acyl CoA synthetase of the plant is supplemented by expression of a transgene encoding an acyl CoA synthetase directed to the peroxisomes. In an alternative embodiment, a CoA transferase targeted to the peroxisomes is utilized instead of an acyl CoA synthetase.

At the extreme 3' end of each transcript, a polyadenylation signal can be engineered. A polyadenylation signal refers to any sequence that can result in polyadenylation of the MRNA in the nucleus prior to export of the mRNA to the cytosol, such as the 3' region of nopaline synthase (Bevan, M., Barnes, W. M. Chilton, M. D. Nucleic Acids Res. 1983, 11, 369-385).

In an alternative embodiment, the genes can be engineered such that expression is achieved from one promoter and one polyadenylation signal. In one embodiment, the genes can be expressed as a polyprotein and cleaved into mature coding sequences via the action of a viral protease (Dasgupta, S., Collins, G. B., Hunt, A. G. The Plant Journal, 1998, 16, 107-116; U.S. Pat. No. 5,846,767). In an alternative embodiment, each coding region is preceded by an internal ribosome entry site allowing translation initiation at multiples sites on one polycistronic mRNA (WO 98/54342).

Selectable marker genes useful in practicing the described invention include the neomycin phosphotransferase gene nptll (U.S. Pat. Nos. 5,034,322, 5,530,196), hygromycin resistance gene (U.S. Pat. No. 5,668,298), and the bar gene encoding resistance to phosphinothricin (U.S. Pat. No. 5,276, 268). EP 0 530 129 A1 describes a positive selection system which enables the transformed plants to outgrow the nontransformed lines by expressing a transgene encoding an enzyme that activates an inactive compound added to the growth media. U.S. Pat. No. 5,767,378 describes the use of mannose or xylose for the positive selection of transgenic plants. Screenable marker genes useful include the β-glucuronidase gene (Jefferson et. al., 1987, EMBO J. 6: 3901-3907; U.S. Pat. No. 5,268,463) and native or modified green fluorescent protein gene (Cubitt et. al., 1995, Trends Biochem Sci. 20: 448-455; Pang et. al., 1996, Plant Physiol. 112:893-900). Some of these markers have the added advantage of introducing a trait e.g. herbicide resistance into the plant of interest providing an additional agronomic value on the input side.

The transformation of suitable agronomic plant hosts using these vectors can be accomplished by a range of methods and plant tissues. Suitable plants include, but are not limited to, biomass crops such as tobacco, alfalfa, and switch grass, and oil seed crops such as maize, soybean, cottonseed, sunflower, palm, coconut, safflower, flax, and peanut, as well as mustards including *Sinapis alba*, and the *Brassica* family including *napus, rappa*, sp. *carinata* and *juncea*. Suitable tissues for transformation using these vectors include protoplasts, cells, callus tissue, leaf discs, pollen, meristems etc. Suitable transformation procedures include *Agrobacterium*-mediated transformation, biolistics, microinjection, electroporation, polyethylene glycol-mediated protoplast transformation, liposome-mediated transformation, silicon fiber-mediated transformation (U.S. Pat. No. 5,464,765) etc. (Gene Transfer to Plants (1995), Potrykus, I. and Spangenberg, G. eds. Springer-Verlag Berlin Heidelberg New York; "Transgenic Plants: A Production System for Industrial and Pharmaceutical Proteins" (1996), Owen, M. R. L. and Pen, J. eds. John Wiley & Sons Ltd. England and Methods in Plant Molecular Biology—a laboratory course manual (1995), Maliga, P., Klessig, D. F., Cashmore, A. R., Gruissem, W. and Varner, J. E. eds. Cold Spring Laboratory Press, New York). The transformation of monocotyledons, such as maize, is described in U.S. Pat. No. 5,591,616.

In order to generate transgenic plants using the constructs, following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene at such that the level of desired polypeptide(s) is obtained in the desired tissue and cellular location.

For the specific crops useful, transformation procedures have been established (Gene Transfer to Plants (1995), Potrykus, I. and Spangenberg, G. eds. Springer-Verlag Berlin Heidelberg New York; "Transgenic Plants: A Production System for Industrial and Pharmaceutical Proteins" (1996), Owen, M. R. L. and Pen, J. eds. John Wiley & Sons Ltd. England and Methods in Plant Molecular Biology—a laboratory course manual (1995), Maliga, P., Klessig, D. F., Cashmore, A. R., Gruissem, W. and Varner, J. E. eds. Cold Spring Laboratory Press, New York) all of which are incorporated herein by reference.

The method disclosed herein can be also used for increasing the levels of C8 and C10 hydroxyacids or fatty acids of a plant oil composition by, for example, a) expressing a transgene encoding an enzyme having the catalytic activity of 3-hydroxyacyl-ACP thioesterase, and b) growing the plant under appropriate conditions for the production of the plant oil composition.

The following examples further illustrate the modification of non-native bacterial PHA producers and plants for medium chain length PHA production from fatty acid biosynthetic pathways.

EXAMPLES

Example 1

Construction of *E. coli* Expression Cassettes for PhaG and PhaC

The gene encoding PhaG was isolated by PCR from *Pseudomonas putida* genomic DNA using primers phaGF-EcorI and phaGR-KpnI and cloned into the EcoR I and Kpn I sites of the *E. coli* expression vector pTRCN forming plasmid pMTX-phaG. The sequence of the phaG insert in pMTX-phaG (SEQ ID NO:9) was found to be identical to the sequence listed in Genbank (Accession #AF052507).

```
                          EcoRI  RBS                  annealing region
Primer phaGF-EcorI 5' ggaattc aggagg ttttt atgaggccagaaatcgctgtacttg 3'   (SEQ ID NO:
                                                                          1)

Kpn I          annealing region
Primer phaGR-KpnI  5' ggggtaccct cagatggcaaatgcatgctgccctgc 3'            (SEQ ID NO:
                                                                          2)
```

Plasmid pSU18-KPS1.2N #3, expressing synthase 1 from *Pseudomonas oleovorans*, was constructed from plasmid pKPS 1.2 using a multi-step procedure as follows. Plasmid pKPS1.2 contains phaC with its native ribosome binding site in vector pKK223-3 (Amersham Pharmacia Biotech, Piscataway, N.J.). The fragment is equivalent to bases 535 to 2241 of the 6.459 kb EcoRI fragment described in WO 91/00917. The PhaC fragment of pKPS1.2 containing flanking BamHI and HindIII sites was subdloned into pTRCN forming pTRCNKPS1.2.SDS-PAGE analysis of crude lysates of *E. coli* expressing pTRCN-KPS 1.2 showed no detectable expression of the synthase.

To further optimize expression of the synthase, an optimal *E. coli* ribosome binding site was placed upstream of the start codon of the synthase using PCR. A 0.43 kb fragment was amplified from plasmid pTRCN-KPS1.2 using primers Posyn1-N and Posyn1-nrSacII and cloned into the EcoRI/SmaI sites of vector pTRCN as an EcoRI/blunt-ended fragment.

```
                EcoRI  RBS                    annealing region
Posyn1-N     5' ccgaattcaggaggttttattatgagtaacaagaacaacgatgagctg 3'   (SEQ ID NO:
                                                                      3)

annealing region
Posyn1-nrSacII 5'ttggtcggagccatggcttcggtcatcagg 3'                    (SEQ ID NO:
                                                                      4)
```

DNA sequencing verified that the wild-type sequence of the PCR fragment had been isolated. The intact synthase gene was reconstructed by subcloning a 1.2 kb C-terminal SacII/HindIII synthase fragment into the SacII/HindIII sites directly behind the PCR fragment forming plasmid pTRCN-KPS1.2N. The DNA sequence of plasmid pTRCN-KPS1.2N is listed in SEQ ID NO:10. (pKPS1.2N). SDS-PAGE analysis of crude lysates of *E. coli* expressing pTRCN-KPS1.2 demonstrated expression of a band at approximately 60 kDa that was not present in crude lysates of the control strain containing vector pTRCN alone.

Plasmid pSU-PhaC$_{P.o.}$trc.PhaG, expressing both PhaC and PhaG from one plasmid was created using the following multi-step cloning procedure. A 1.64 kb EcoRI/HindIII fragment containing a strong *E. coli* ribosome binding site and the entire coding region of the synthase was isolated from plasmid pTRCN-KPS1.2N and cloned into the EcoRI and HindIII sites of pSU18 forming plasmid pSU18-KPS1.2N #3. Vector pSU18 is a medium copy number plasmid derived from pSU2718 (Martinez, E.; Bartolome, B.; de la Cruz, F. Gene 1988, 68, 159) and contains the p15A origin of replication and chloramphenicol resistance marker. A fragment encoding the trc promoter and phaG from plasmid pMTX-phaG was inserted into pSU18-KPS1.2N #3 as follows. A 1.002 kb fragment was generated by PCR, using primer trc-PhaG.c, primer trc-PhaG.r, and template pMTX-PhaG, and cloned into the HindIII sites of pSU18-KPS1.2N #3. The resulting plasmid pSU-PhaC$_{P.o.}$trc.PhaG, contains phaC behind the lac promoter of pSU18 and phaG behind the trc promoter. The sequence of the PhaC$_{P.o.}$trc.PhaG insert for plasmid pSU-PhaC$_{P.o.}$trc.PhaG is listed in SEQ ID NO: 11.

C. overnight. The starter cultures were diluted (1:100) into LB medium (5 mL) containing ampicilin and chloramphenicol and grown for 10 hours at 30° C. with agitation at 250 RPM. The cultures were harvested and the cells were washed two times with 2.5 mLs of medium E salts (Vogel, H. J. and Bonner, D. M., J. Biol. Chem. 1956, 218, 97-106). Cell pellets were resuspended in 2.5 mL of medium E salts and 1 mL of the suspension was used to inoculate flasks for gene expression. Cultures were performed in 500 mL Erlenmeyer flasks containing 100 mL Medium E salts, 1.5% glucose, 1 mg/L thiamine, 100 mg/L ampicillin, and 25 mg/L chloramphenicol. The flasks were incubated at 30° C. until the absorbance at 600 nm reached 0.4. Gene expression was induced with 0.4 mM IPTG and the flasks were incubated at 30° C. for an additional 48 hours before harvest.

Cells were separated from the culture supernatants by centrifugation at 12,000 g. Cell pellets were washed two times with 25 mLs of medium E salts and dried overnight in a lyophilizer. A portion of the cell supernatant (3 mL) was frozen in liquid $N_2$ and evaporated to dryness in a lyophilizer. Cell pellets, cell supernatant samples, and 3-hydroxyalkanoic acid standards (3-hydroxyhexanoate, 3-hydroxyoctanoate, 3-hydroxydecanoate, 3-hydroxydodecanoate) were prepared for analysis by gas chromatography by converting them to the corresponding butyl esters as follows. An aliquot (2 mL) of a butanolysis reagent [9 parts butanol: 1 part HCl: 1 mg/mL internal standard methylbenzoic acid] was added to the samples in a screw top vial and the samples were incubated at 110° C. for 2 hours. The vials were cooled and water (3 mL) was added. The samples were vortexed and the aqueous and organic layers were separated by centrifugation in a table top

```
                  HindIII        annealing region
trc-PhaG.c  5' cccaagcttTttgacaattaatcatccggctcgtataatg (SEQ ID NO:
                                                        5)

HindIII        annealing region
trc-PhaG.r  5' cccaagctttcagatggcaaatgcatgctgccctctg     (SEQ ID NO:
                                                        6)
```

Example 2

Production of 3-Hydroxyoctanoic Acid and 3-Hydroxydecanoic Acid in Recombinant *E. coli* Strains Expressing PhaG and PhaC In an attempt to produce PHA in *E. coli* using glucose as a carbon source, host strain JM109 (Promega, Madison, Wis.) was transformed with plasmids selected from the following group: pSU-PhaC.$_{P.o.}$trc.PhaG (medium chain length synthase and PhaG expression plasmid), pSU18 (control vector for pSU-PhaC.$_{P.o.}$trc.PhaG), and pTRCN (plasmid into which additional genes could be inserted). Starter cultures (5 mL) of JM109/pTRCN/pSU18 and JM109/pSU-PhaC.$_{P.o.}$trc.PhaG were inoculated with a single colony into LB medium (Difco) containing ampicilin (100 mg/L) and chloramphenicol (25 mg/L). The cultures were grown at 30° centrifuge. An aliquot of the organic phase (1 µmL) was analyzed on a SPB-1 fused silica capillary GC column (30 m; 0.32 mm ID; 0.25 µm film; Supelco; Bellefonte, Pa.) connected to a Hewlett Packard gas chromatograph using a split ratio of 1:50 and a flow rate of 2 mL/min. The temperature profile for the analysis was as follows: 80° C., 2 min; 10° C. per min to 250° C.; 250° C., 2 min.

GC analysis of whole cell pellets of strains JM109/pSU-PhaC.$_{P.o.}$trc.PhaG/pTRCN, expressing PhaC and PhaG, and JM109/pSU18/pTRCN, containing only control vectors, did not yield any peaks corresponding to butyl esters of PHA monomer units. However, peaks possessing retention times comparable to butyl 3-hydroxyoctanote and butyl 3-hydroxydecanoate were observed in GC chromatograms of JM109/pSU-PhaC.$_{P.o.}$trc.PhaG supernatants that had been derivitized by butanolysis. The peaks were found to contain 0.14 mM butyl 3-hydroxyoctanote and 0.32 mM butyl 3-hydroxydecanoate upon comparison to peaks containing known quantities of 3-hydroxyoctanoic acid and 3-hydroxydecanoic acid that had been derivitized by butanolysis (Table 1). Culture supernatants from strain JM109/pSU18/pTRCN did not contain any peaks corresponding to butyl esters of 3-hydroxyacids (Table 1).

Example 3

Construction of E. coli Expression Cassette for PhaG, PhaC, and Acyl CoA Synthetase (AlkK)

A PhaG catalyzed conversion of 3-hydroxyacyl ACPs to free fatty acids (FIG. 1, Route B) instead of 3-hydroxyacyl CoAs (FIG. 1, Route A) could provide one explanation for the observation of 3-hydroxyacyl butyl esters in GC chromatograms of derivitized culture supernatants from E. coli strains expressing PhaG and PhaC. In the E. coli accumulation studies described in Example 2, the native E. coli acyl CoA synthetase may not have been induced in the minimal medium growth conditions employed due to repression of transcription of the gene encoding the acyl CoA synthetase (fadD) by FadR, an E. coli protein that functions as a transcriptional regulator (Black, P. N., DiRusso, C. C., Metzger, A. K., Heimert, T. L. J. Biol. Chem. 1992, 267, 25513-25520). Alternatively, FadD may not have substrate specificity for medium chain length 3-hydroxy fatty acids.

To test whether the addition of an acyl CoA synthetase would promote polymer formation, a cytosolic acyl-CoA synthetase, encoded by alkK, (van Beilen, J. B.; Eggink, G.; Enequist, H.; Bos, R.; Witholt, B. Mol. Microbiol. 1992, 6, 3121-3136) was amplified from *Pseudomonas oleovorans* genomic DNA using primers Posynrbs.c and Posynrbs.r.

sion was induced with 0.4 mM IPTG and the flasks were returned to 30° C. for four hours. The cells were collected by centrifugation, resuspended in 10 mM Tris-Cl buffer (pH 7.5), and were disrupted by sonication. Acyl CoA synthetase activity was estimated by monitoring the consumption of coenzyme A at 410 nm using Ellman's reagent [5,5'-dithiobis (2-nitrobenzoic acid); DTNB] (Ellman, G. L. 1959, Arch. Biochem. Biophys. 82 70-77). The assay mixture (500 µL) contained 200 mM $KH_2PO_4$ (pH 7), 7.5 mM CoA, 3.75 mM ATP, 5 mM $MgCl_2$, 4.2 mM fatty acid and enzyme. Octanoic acid and 3-hydroxyoctanoic acid were used as the fatty acid substrates in the reaction. The reaction was performed at room temperature and initiated by the addition of enzyme. Aliquots (10 µl) were removed every 30 seconds and quenched in 140 µl of 5% trichloroacetic acid. Precipitated proteins were removed by centrifugation in a microcentrifuge for 1 min. and an aliquot (100 µl) of the supernatant was diluted in 690 µl of 500 mM KPi (pH 7.4). An aliquot of DTNB stock [10 µl of a 10 mM stock solution in 500 mM KPi (pH 7.4)] was added and the samples were incubated at room temperature for two minutes. The amount of CoA consumed at each timepoint of the reaction was quantitated from the absorbance values at 410 nm ($\epsilon$=13.7 $mM^{-1}$ $cm^{-1}$) (FIGS. 2 and 3).

Strain DH5α/pTRCN-AlkK possessed 0.22 U/mg of activity when assayed for acyl CoA synthetase activity in the presence of octanoic acid using the enzyme assay procedure described above. Control strain DH5α/pTRCN contained 0.00081 U/mg of activity. When assayed in the presence of 3-hydroxyoctanoic acid, DH5α/pTRCN-AlkK possessed

```
          EcoRI    RBS                   annealing region
Posynrbs.c 5' ggaattcaggaggttttttgttaggtcagatgatgcgtaatcag 3'    (SEQ ID NO: 7)

BamHI             annealing region
Posynrbs.r 5' cgggatccttattcacagacagaagaactactgcg 3'             (SEQ ID NO: 8)
```

The PCR product was digested with EcoRI and BamHI and cloned into the EcoRI and BamHI sites of the expression vector pTRCN forming plasmid pTRCNalkK. The sequence of alkK in the bacterial expression construct pTRCNalkK is shown in SEQ ID NO:12. Comparison of the PCR product to the sequence of alkK in Genbank (Genbank Accession #X65936) revealed two differences. A "t" was observed instead of a "c" (346 bases from the "A" of the "ATG") resulting in phenylalanine instead of leucine in the coding sequence. A "g" was observed instead of an "a" (386 bases from the "A" of the "ATG") resulting in the observance of an arginine in the coding sequence instead of a histidine. Six separate PCR products contained both sequence discrepancies suggesting they were not mutations introduced by PCR but were reflective of the true coding sequence of the gene used as the template in the PCR reaction.

The acyl CoA synthetase activity of AlkK was estimated using the following procedure. Five mL starter cultures of DH5α/pTRCN and DH5α/pTRCN-AlkK were prepared in 2XYT containing 100 mg/L ampicillin. The cultures were incubated with shaking at 30° C. for 16 hours. The culture was diluted 1 to 100 into 100 mL of 2XYT in a 250 mL Erlenmeyer flask and the cells were incubated at 30° C. until the absorbance at 600 nm was approximately 0.6. Gene expres- 0.21 U/mg of activity compared to the 0.00063 U/mg observed in control strain DH5α/pTRCN.

Example 4

Production of Medium Chain Length PHAs in *E. coli* Expressing PhaC, PhaG, and AlkK To test whether the presence of a cytosolic acyl CoA synthetase enabled polymer production in *E. coli* strains expressing PhaG and PhaC, strain JM 109/pSU-PhaC.$_{P.o.}$trc.PhaG/ pTRCN-AlkK was prepared for polymer accumulation studies as described in Example 2. GC chromatograms of whole cells derivitized by butanolysis contained 2.2% dry cell weight polymer composed of 20.1 mol % 3-hydroxy octanoic acid and 79.9 mol % 3-hydroxy decanoic acid (Table 1). The presence of 3-hydroxy butyl esters in GC chromatograms of JM109/pSU-PhaC.$_{P.o.}$trc.PhaG/pTRCN-AlkK supernatants decreased significantly compared to GC chromatograms of JM109/pSU-PhaC.$_{P.o.}$trc.PhaG cell supernatants yielding 0.16 mM of butyl 3-hydroxydecanoate and no butyl 3-hydroxy octanoate (Table 1). The requirement of supplemental acyl CoA synthetase activity in *E. coli* for polymer production suggests that PhaG only possesses 3-hydroxy acyl ACP thioesterase activity in vivo (FIG. 1, Route B).

To determine if FadR regulation of acyl CoA synthetase transcription prevented the expression of acyl CoA synthetase in the experiments described in Example 2, the FadR⁻ strain LS5218 [fadR 601, atoC 512 (con); CGSC strain# 6966; *E. coli* Genetic Stock Center, Yale University] was used as a host strain for polymer accumulation studies. Strains LS5218/pSU18 (control strain) and LS5218/pSU-PhaC.$_{P.o.}$trc.PhaG (PhaC and PhaG expression strain) were prepared and cultured as described in Example 2 with the exception that 0.4% glucose was used as the carbon source in all experiments involving LS5218. Strain LS5218/pSU-PhaC.$_{P.o}$trc.PhaG (PhaC and PhaG expression strain) produced 4.5% dry cell weight of polymer consisting of 9.9 mol % 3-hydroxy octanoic acid and 90.1 mol % 3-hydroxy decanoic acid (Table 1). No medium chain length 3-hydroxy acids were observed in the culture supernatant (Table 1). Strain LS5218/pSU18 (control strain) did not produce intracellular accumulations of polymer and did not excrete medium chain length hydroxy acids into the culture supernatant (Table 1). These results suggest FadR regulation of acyl CoA synthetase transcription may have prevented the expression of the native acyl CoA synthetase in strain JM109/pSU-PhaC. $_{P.o}$trc.PhaG (Example 2) preventing polymer formation.

351), the gene encoding PhaG, and the alfalfa rubisco termination sequence (Kiloudi, H., Vézina, L. -P., Mercier, J., Castonguay, Y., Allard, G., Laberge, S. 1997. Gene 197 : 343-351) followed by an expression cassette encoding the alfalfa rubisco promoter, the alfalfa rubisco chloroplast targeting signal, the gene encoding PhaC1 from *Pseudomonas aeroginosa* (Timm, A. & Steinbuchel, A. J. Appi. Microbiol. 1992, 209, 15-30), and the alfalfa rubisco termination sequence.

Plasmid pBI-C4PPDK.PhaG.Rbc.PhaC (FIG. 4B) is a derivative of the plant transformation vector pBI10 (Clontech, Palo Alto, Calif.) and contains an expression cassette encoding the 35S-C4PPDK promoter (Sheen, J. EMBO 1993, 12, 3497-3505), the pea rubisco chloroplast targeting signal including DNA encoding the N-terminal 24 amino acids of the pea rubisco protein (Cashmore, A. R., 1983, in Genetic Engineering of plants, eds Kosuge, T., Meredith, C. P. & Hollaender, A. (Plenum, New York), p 29-38; Nawrath, C., Poirier, Y. and Somerville, C., 1994, *PNAS.* 91 :12760-12764), and the Nos termination sequence (Bevan, M.; Barnes, W. M.; Chilton, M -D. Nucleic Acids Research 1983, 11, 369-385), followed by an expression cassette encoding the alfalfa rubisco promoter, the alfalfa rubisco chloroplast targeting signal, the gene encoding PhaC1 from *Pseudomonas aeroginosa*, and the alfalfa rubisco termination sequence.

TABLE 1

Concentration of 3-hydroxyacyl butyl esters observed.$^{a}$

| | | | | | 3-Hydroxy Acyl Butyl Esters (mM) in Derivitized Cell Supernatants | |
|---|---|---|---|---|---|---|
| | | PHA | PHA Composition | | | |
| | Glucose | Content | (mol %) | | | 3-OH |
| Strain | Content | (% DCW) | 3-OH C8 | 3-OH C10 | 3-OH C8 | C10 |
| JM109/pSU18/pTRCN | 1.5% | — | — | — | — | — |
| *A | 1.5% | — | — | — | 0.14 | 0.32 |
| *B | 1.5% | 2.2 | 20.1 | 79.9 | $^{b}$ | 0.11 |
| LS5218/pSU18 | 0.4% | — | — | — | — | — |
| *C | 0.4% | 4.5 | 9.9 | 90.1 | — | — |

*A: JM109/pSU-PhaC. $_{P_o}$trc.PhaG/pTRCN
*B: JM109/pSU-PhaC. $_{P_o}$.trc.PhaG/pTRCN-AlkK
*C: LS5218/pSU-PhaC. $_{P_o}$trc.PhaG
$^{a}$Observed by gas chromatography in derivitized culture supernatant and cell samples. Supernatant samples were lyophilized, derivitized with butanolysis reagent, and injected on a gas chromatograph. 3-hydroxyacyl butyl esters in the samples were quantitated by butanolysis derivitization of known amounts of standard samples of 3-hydroxy fatty acids.
$^{b}$A small amount of compound is detected but is not quantifiable.

Example 5

Construction of Plant Vectors for Chloroplast-Specific Expression of PhaG and PhaC and Transformation of *Arabidopsis thaliana*

Figure 4B:
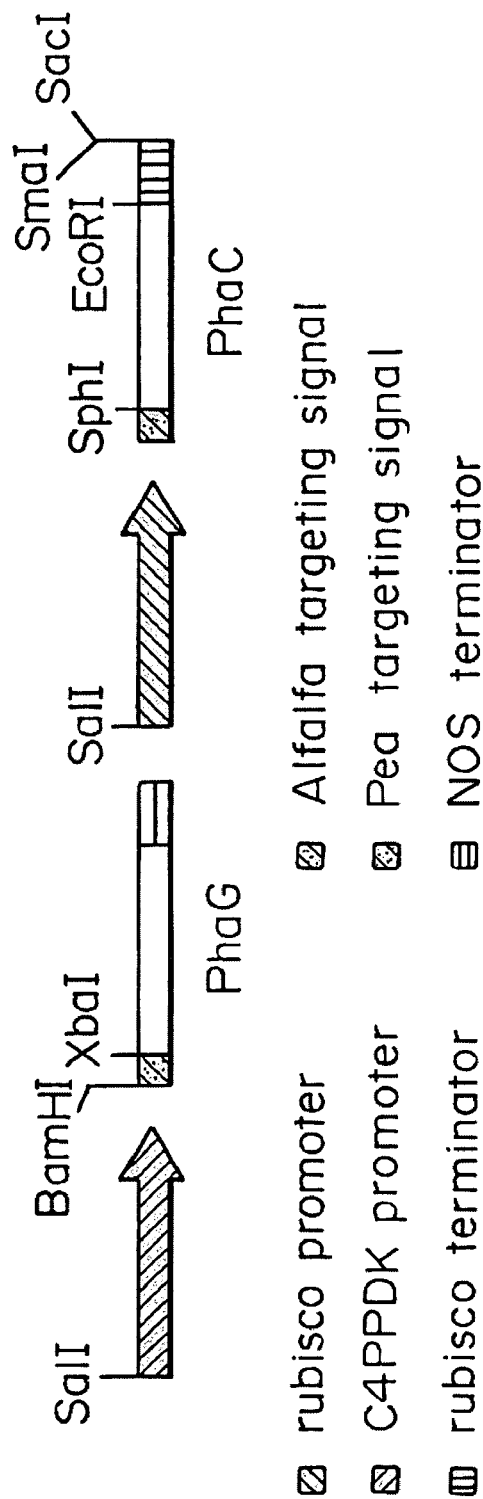
FIG. 4B shows the map of insert in pBI-C4PPDK.PhaG.Rbc.PhaC containing the 35S-C4PPDK promoter, the pea rubisco chloroplast targeting signal including DNA encoding the N-terminal 24 amino acids of the pea rubisco protein, a fragment encoding PhaG, the Nos termination sequence, the alfalfa rubisco promoter fused to the alfalfa chloroplast targeting signal, a fragment encoding PhaC from *Pseudomonas aeroginosa*, and a fragment encoding the alfalfa rubisco termination sequence.

Constructs for the expression of phaG and phaC were prepared for transformation to determine if PhaG and PhaC in plant chloroplasts led to PHA production (FIGS. 4A and 4B).

Plasmid pCambia-Rbc.PhaG.PhaC1 (FIG. 4A) is a derivative of the plant transformation vector pCambia 2300 (Center for the Application of Molecular Biology to International Agriculture, Canberra, Australia) and contains an expression cassette encoding the alfalfa rubisco promoter (Khoudi, H., Vézina, L. -P., Mercier, J., Castonguay, Y., Allard, G., Laberge, S. 1997. Gene 197:343-351), the alfalfa rubisco chloroplast targeting signal (Khoudi, H., Vézina, L. -P., Mercier, J., Castonguay, Y., Allard, G., Laberge, S. 1997. Gene 197:343-

Plasmids were transformed into *Arabidopsis thaliana* with Agrobacterium strain GV3101/pMP90 (Konz, C. & Schell, J. Mol. Gen. Genet. 1986, 204, 383-396) using the *Agrobacterium*-mediated floral dip procedure of Clough and Bent (Clough, S. J. & Bent, A. F. Plant Journal, 1998, 16, 73 5-743). Seeds were isolated from mature siliques and were plated on selection medium containing ½× Murashige Minimal Organics Medium (Life Technologies, Rockville, Md.), 0.7 % agar, 1× Gamborg's B5 vitamins (Sigma, St. Louis, Mo.), and 50 µg/mL kanamycin. After 7 days, green seedlings, resistant to kanamycin selection, and white seedlings, sensitive to kanamycin selection, appeared on the plates. The green seedlings were transferred to soil and allowed to mature.

For polymer analysis, leaves from mature plants (approximately 6 weeks old) were harvested and lyophilized. Dried tissues (30-150 mg) were ground and an aliquot of hexane (2 to 5 mLs) was added to each tube. The samples were heated at 70° C. for four hours with occasional vortexing. The hexane fraction was separated from the solid cell material by centrifugation and transferred to a clean tube. The residual cell debris in the tube was washed with an additional aliquot (1 mL) of hexane and the hexane wash was pooled with the hexane fraction from the previous step.

The hexane fraction was further purified by extraction (two times) with one volume of a saturated solution of $NaHCO_3$ followed by extraction with one volume of $H_2O$. The hexane fraction (Fraction A) was evaporated to dryness at 70° C. in a hood. Bicarbonate phases from the previous step were pooled, acidified to pH 2 with HCl, extracted with one volume of hexane, and the resulting hexane layer (Fraction B) was evaporated to dryness at 70° C. in a hood.

Samples from Fractions A and B, as well as samples of 3-hydroxyalkanoic acid standards (3-hydroxyhexanoate, 3-hydroxyoctanoate, 3-hydroxydecanoate, 3-hydroxydodecanoate), were prepared for analysis by gas chromatography by converting them to the corresponding butyl esters as previously described in example 2. GC chromatograms of Fractions A and B prepared from 66 transgenic *Arabidopsis* plants transformed with pCambia-Rbc.PhaG.PhaC1 and 9 transgenic *Arabidopsis* plants transformed with pBI-C4PPDK.PhaG.Rbc.PhaC contained no traces of polymer or monomer. Polymer, if present, was expected in Fraction A whereas monomer, if present, was expected in Fraction B. RT-PCR of leaves from twelve transgenic plants transformed with pBI-C4PPDK.PhaG.Rbc.PhaC and eight transgenic plants transformed with pCambia-Rbc.PhaG.PhaC1 was performed using the ProSTAR HF Single-Tube RT-PCR kit (Stratagene, La Jolla, Calif.) for reverse transcriptase-polymerase chain reactions. Four of the twelve pBI-C4PPDK.PhaG.Rbc.PhaC plants contained transcripts of the size expected for both phaG and phaC (Table 2). Zero of eight pCambia-Rbc.PhaG.PhaC1 plants analyzed contained products of the size expected for both phaG and phaC although several plants contained transcripts for either phaG or phaC (Table 2).

TABLE 2

Results of RT-PCR reactions performed on a RNA sample from a control plant

| Construct | Transformation Isolate | Presence of RNA Transcripts by RT-PCR | |
|---|---|---|---|
| | | PhaG | phaC |
| pBi-C4PPDK-phaG.Rbc.phaC | 1 A | + | + |
| | 2 A | + | + |
| | 2 B | + | + |
| | 4 A | + | − |
| | 4 B | + | − |
| | 5 D | + | + |
| | 7 A | + | − |
| | 7 B | + | − |
| | 8 A | + | − |
| | 8 E | + | − |
| | 10 C | + | − |
| | 11 A | + | − |
| pCambia-RBc.PhaG.PhaC | 1 B | − | + |
| | 2 C | − | + |
| | 3 A | − | + |
| | 3 B | − | − |
| | 3 C | − | + |
| | 4 C | − | + |
| | 8 A | − | − |
| | 19 D | + | − |

Example 6

Plant Expression Cassettes for PHA Production in the Chloroplasts of Leaves or the Plastids of Seeds using PhaG, PhaC and AlkK The inability of *Arabidopsis thaliana* to produce PHA in chloroplasts despite the successful production of RNA transcripts for phaG and phaC suggests that plant chloroplasts may be unable to complete a 3-hydroxy acyl ACP-CoA transferase reaction successfully when PhaG is expressed in the chloroplasts. Supplementation of the 3-hydroxy acyl ACP thioesterase activity of PhaG with an acyl CoA synthetase possessing activity on medium chain length 3-hydroxy acids may enable the successful formation of 3-hydroxy acyl CoAs for PHA synthesis.

The sequence of alkK in the plant expression construct pUC-C4PPDK.TS.AlkK is shown in SEQ ID NO:13. The sequences "tctaga" (SEQ ID NO:14) and "ggtacc" (SEQ ID NO:15) are XbaI and KpnI restriction sites, respectively, introduced for cloning purposes. Plasmid pUC-C4PPDK.TS.AlkK was used as a starting plasmid to create other plant expression constructs containing alkK.

For PHA production in the chloroplasts of leaves, plasmid pCambia-C4PPDK.TS.PhaG.TS.AlkK.TS.PhaC$_{P.o}$ (FIG. 5A) was designed. Plasmid pCambia-C4PPDK.TS.PhaG.TS.AlkK.TS.PhaC$_{P.o}$ contains the 35S-C4PPDK promoter, the pea rubisco chloroplast targeting signal including DNA encoding the N-terminal 24 amino acids of the pea rubisco protein, a fragment encoding PhaG, a Nos termination sequence, the 35S-C4PPDK promoter, the pea rubisco chloroplast targeting signal including DNA encoding the N-terminal 24 amino acids of the pea rubisco protein, a fragment encoding AlkK, a Nos termination sequence, the 35S-C4PPDK promoter, the pea rubisco chloroplast targeting signal including DNA encoding the N-terminal 24 amino acids of the pea rubisco protein, a fragment encoding PhaC from *Pseudomonas oleovorans* and a Nos termination sequence.

Plasmid pCambia-C4PPDK.TS.PhaG.TS.AlkK.TS.PhaC$_{P.o}$ can be transformed into *Arabidopsis*, as previously described in Example 5, or Tobacco, as described in the following procedure. In a laminar flowhood under aseptic conditions, leaves from a tobacco plant are sterilized for 15 minutes in a one liter beaker containing a solution of 10% bleach and 0.1% Tween 20. The sterilized leaves are washed in one liter of water for 10 minutes, the water is decanted, and the washing step is repeated two additional times. The intact part of the leaves are cut in small pieces with a scalpel, avoiding any injured areas of the leaves. An aliquot (20 mL) of MS-suspension is mixed with 5 mL of an overnight culture of *Agrobacterium* strain GV3101/pMP90 (Konz, C. & Schell, J. Mol. Gen. Genet. 1986, 204, 383-396) carrying the construct to be transformed [MS-suspension contains (per L) 4.3 g MS salts, 1 mL of B5 vitamins (Sigma, St. Louis, Mo.), 30 g sucrose, 2 mg p-chlorophenoxyacetic acid, and 0.05 mg kinetin, pH 5.8]. The tobacco leaf pieces are introduced into the solution and vortexed for a few seconds. The leaves are removed, wiped on sterile filter paper, and placed in a petri dish to remove the excess *Agrobacterium* solution. An aliquot (1 mL) of tobacco cell culture is added on top of solidified MS-104 medium in a petri dish and a sterile piece of filter paper is placed directly on the top of the culture [MS-104 medium contains (per L) 4.3 g MS salts, pH 5.8, 1 mL B5 vitamins, 30 g sucrose, 1 mg benzylaminopurine, 0.1 mg napthalene acetic acid, and 8 g of phytagar]. The tobacco leaf pieces are placed on top of the filter and incubated for two days at 25° C. The leaf pieces are transferred, face-up, to a petri dish containing MS-selection medium and gently pressed into the medium [MS-selection medium contains (per L) 4.3 g MS salts, pH 5.8, 1 mL B5 vitamins, 30 g sucrose, 1 mg benzylaminopurine, 0.1 mg napthalene acetic acid, 500 mg of carbenicillin, 50 mg kanamycin, and 6.5 g of phytagar]. The dishes are wrapped with parafilm and incubated at 25° C. for 3 weeks. The leaves are transferred to fresh MS-selection medium and incubation at 25° C. is continued until plantlets appeared. Plantlets are separated from the callus and placed in test-tubes (24×3 cm) containing 10 mL of MS-rooting medium [MS-rooting medium contains (per L) 4.3 g MS salts, pH 5.8, 1 mL B5 vitamins, 30 g sucrose, and 6.5 g of phytagar]. When roots reach 1 cm in length, the transformed plants are transferred to soil and covered with an inverted, transparent, plastic cup in which a hole has been pierced in the bottom. After 4 or 5 days, the cup is removed and transformed tobacco plants are grown in a Percival Scientific *Arabidopsis* Growth Chamber (23° C., 70% humidity, 16 hour days, 8 hour nights). Leaves from transgenic tobacco plants can be analyzed for polymer using the extraction procedures previously described in Example 5 for transgenic *Arabidopsis* plants.

Figure 6A:
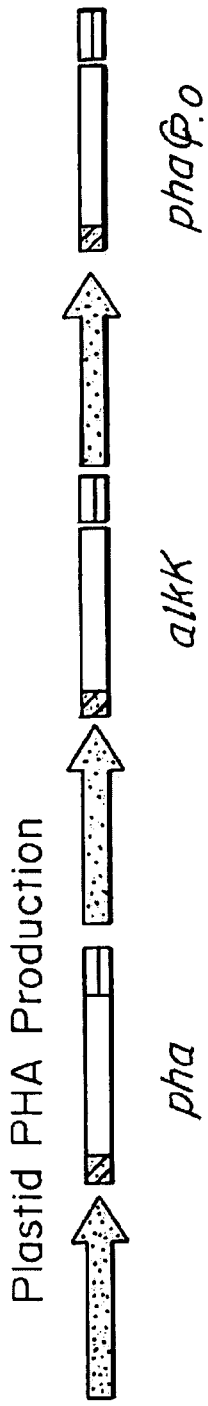
FIG. 6A is the map of inserts in the plant transformation vector for seed-specific expression of phaG, alkK and phaC for the accumulation of polymer in the plastids of seeds.

For seed specific, plastid based, PHA production, a plasmid containing a seed specific promoter, a plastid targeting signal fused to PhaG, a poly adenylation signal, a seed specific promoter, a plastid targeting signal fused to AlkK, a poly adenylation signal, a seed specific promoter, a plastid targeting signal fused to PhaC, and a poly adenylation signal can be constructed (FIG. 6A). Seed specific promoters such as the napin gene promoter (U.S. Pat. Nos. 5,420,034; 5,608,152), the acetyl-CoA carboxylase promoter (U.S. Pat. Nos. 5,420,034; 5,608,152), 2S albumin promoter, seed storage protein promoter, phaseolin promoter (Slightom et. al., 1983, Proc. Natl. Acad. Sci. USA 80: 1897-1901), oleosin promoter (plant et. al., 1994, Plant Mol. Biol. 25: 193-205; Rowley et. al., 1997, Biochim. Biophys. Acta.1345: 1-4; U.S. Pat. No. 5,650,554; PCT WO 93/20216), zein promoter, glutelin promoter, starch synthase promoter, starch branching enzyme promoter etc are useful for constructing the seed specific, plastid based, PHA production construct.

The seed specific, plastid based, PHA production construct can be transformed into *Arabidopsis* as described in Example 5. Alternatively, the construct can be transformed into *Brassica napus* using the following procedure (Moloney M. M., Walker J. M., Sharma K. K. Plant Cell, 1989, 8, 238-242). Seeds of *Brassica napus* cv. Westar are surfaced sterilized in 10% commercial bleach (Javex, Colgate-Palmolive Canada Inc.) for 30 min with gentle shaking. The seeds are washed three times in sterile distilled water. Seeds are placed on germination medium comprising Murashige-Skoog (MS) salts and vitamins, 3% sucrose and 0.7% phytagar, pH 5.8 at a density of 20 per plate and maintained at 24° C. in a 16 h light/8 h dark photoperiod at a light intensity of 60-80 $\mu m^{-2} s^{-1}$ for 4-5 days. Constructs, are introduced into *Agrobacterium tumefaciens* strain EHA101 (Hood E E, Helmer G L, Fraley R. T., Chilton M. D., J. Bacteriol. 1986, 168, 1291-1301) by electroporation. Prior to transformation of cotyledonary petioles, single colonies of strain EHA101 harboring each construct are grown in 5 mL of minimal medium, supplemented with the appropriate selection antibiotics for the transformation vector, for 48 h at 28° C. One mL of bacterial suspension is pelleted by centrifugation for 1 min in a microfuge. The pellet is resuspended in 1 mL minimal medium.

For transformation, cotyledons are excised from 4 to 5 day old seedlings so that they included ~2 mm of petiole at the base. Individual cotyledons with the cut surface of their petioles are immersed in diluted bacterial suspension for 1 s and immediately embedded to a depth of ~2 mm in co-cultivation medium, MS medium with 3% sucrose and 0.7% phytagar, enriched with 20 µM benzyladenine. The inoculated cotyledons are plated at a density of 10 per plate and incubated under the same growth conditions for 48 h. After co-cultivation, the cotyledons are transferred to regeneration medium comprising MS medium supplemented with 3% sucrose, 20 µM benzyladenine, 0.7% phytagar, pH 5.8, 300 mg/L timentinin and the appropriate antibiotics for selection of the plant transformation vector.

After 2-3 weeks regenerant shoots are obtained, cut, and maintained on 'shoot elongation' medium (MS medium containing 3% sucrose, 300 mg/L timentin, 0.7% phytagar and the appropriate antibiotic) in Magenta jars. The elongated shoots are transferred to 'rooting' medium comprising MS medium, 3% sucrose, 2 mg/L indole butyric acid, 0.7% phytagar and 500 mg/L carbenicillin. After the emergence of roots, plantlets are transferred to potting mix (Redi Earth, W. R. Grace and Co. Canada Ltd.). The plants are maintained in a misting chamber (75% relative humidity) under the same growth conditions.

Example 7

Plant Expression Cassettes for PHA Production in the Cytosol of Leaves or Seeds using PhaG, PhaC and AlkK Expression of a 3-hydroxy acyl ACP thioesterase activity in chloroplasts or plastids should lead to a diversion of carbon from fatty acid biosynthesis producing 3-hydroxy fatty acids. Since chloroplasts and plastids do not normally accumulate 3-hydroxy fatty acids, the molecules should be exported from the organelle and either incorporated into triacylglycerides or transported to the peroxisomes for degradation. The incorporation of medium chain length 3-hydroxy acids into triacylglycerides in the seeds of oil seed crops would produce novel seed oils. The presence of a cytosolic acyl CoA synthetase and a cytosolic PHA synthase could convert the medium chain 3-hydroxy fatty acids in the cytosol to medium chain length PHAs.

Plasmid pCambia-C4PPDK.TS.PhaG.AlkK.PhaC$_{P.o.}$ (FIG. 5B) is a plant transformation vector designed for cytosolic PHA production. It encodes sequences for leaf-specific expression of PhaG in the chloroplasts, and leaf-specific expression of AlkK and PhaC in the cytosol. Plasmid pCambia-C4PPDK.TS.PhaG.AlkK.PhaC$_{P.o}$ contains the 35S-C4PPDK promoter, the pea rubisco chloroplast targeting signal including DNA encoding the N-terminal 24 amino acids of the pea rubisco protein, a fragment encoding PhaG, a Nos termination sequence, the 35S-C4PPDK promoter, a fragment encoding AlkK, a Nos termination sequence, the 35S-C4PPDK promoter, a fragment encoding PhaC from *Pseudomonas oleovorans* and a Nos termination sequence. Plasmid pCambia-C4PPDK.TS.PhaG.AlkK.PhaCp$_{P.o.}$ can be transformed into Arabidopsis or Tobacco as described in previous examples.

Figure 6B:
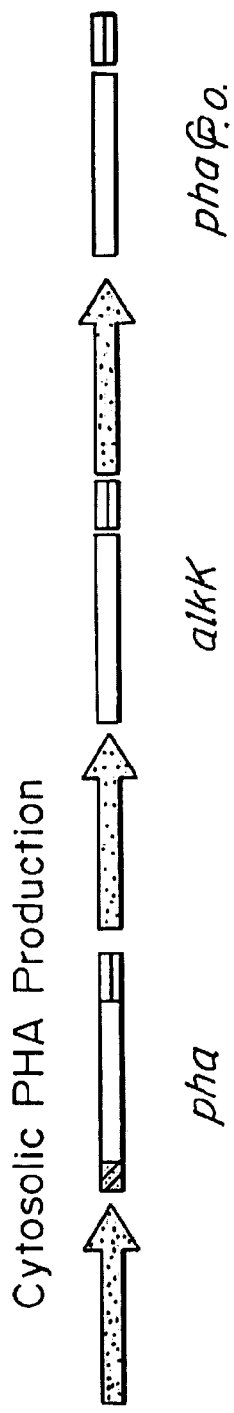
FIG. 6B is the map of inserts in the plant transformation vector for seed-specific expression of phaG, alkK and phaC for the accumulation of polymer in the cytosol of seeds.

For seed specific, cytosolic PHA production, a plasmid containing a seed specific promoter, a plastid targeting signal fused to PhaG, a poly adenylation signal, a seed specific promoter, a fragment encoding AlkK, a poly adenylation signal, a seed specific promoter, a fragment encoding PhaC, and a poly adenylation signal can be constructed (FIG. 6B). The seed specific, cytosolic PHA production construct can be transformed into *Arabidopsis* or oil seed crops such as *Brassica napus* as described in the previous examples.

Example 8

Plant Expression Cassettes for PHA Production in the Peroxisomes of Leaves or Seeds using PhaG, PhaC and AlkK Since a portion of the medium chain length 3-hydroxy fatty acids exported from chloroplasts or plastids may enter the peroxisomes for degradation, targeting of an acyl CoA synthetase and a PHA synthase to the peroxisomes of leaves or seeds could yield PHA. Plasmid pCambia-C4PPDK.TS.PhaG.AlkK.perox.PhaC$_{P.o.}$perox. (FIG. 5B) is a plant transformation vector designed for leaf-based peroxisomal PHA accumulation. The construct contains the 35S-C4PPDK promoter, the pea rubisco chloroplast targeting signal including DNA encoding the N-terminal 24 amino acids of the pea rubisco protein, a fragment encoding PhaG, a Nos termination sequence, the 35S-C4PPDK promoter, a fragment encoding AlkK fused to a C-terminal peroxisomal targeting signal composed of the C-terminal 34 amino acids of *Brassica napus* isocitrate lyase (Olsen, L. J., Ettinger, W. F., Damsz, B., Matsudaira, K., Webb, M. A., Harada, J. J. 1993, Plant Cell, 5, 941-952), a Nos termination sequence, the 35S-C4PPDK promoter, a fragment encoding PhaC from *Pseudomonas oleovorans* fused to a C-terminal peroxisomal targeting signal composed of the C-terminal 34 amino acids of *Brassica napus* isocitrate lyase, and a Nos termination sequence. Plasmid pCambia-C4PPDK.TS.PhaG.AlkK.perox.PhaC$_{P.o.}$ perox can be transformed into *Arabidopsis* or Tobacco as described in previous examples.

Figure 6C:
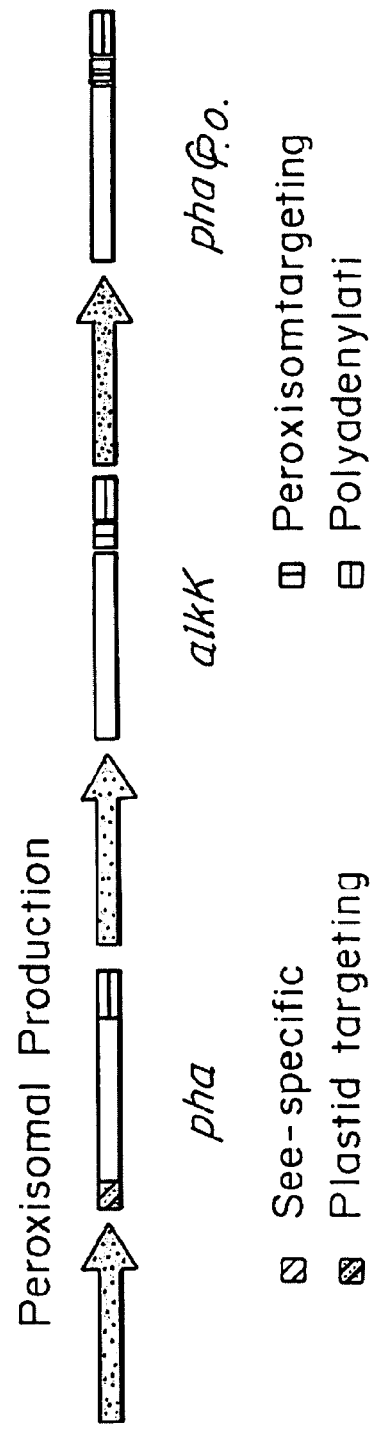
FIG. 6C is the map of inserts in the plant transformation vector for seed-specific expression of phaG, alkK and phaC for the accumulation of polymer in the peroxisomes of seeds.

For seed specific, peroxisomal PHA production, a plasmid containing a seed specific promoter, a plastid targeting signal fused to PhaG, a poly adenylation signal, a seed specific promoter, a fragment encoding AlkK fused to a peroxisomal targeting signal, a poly adenylation signal, a seed specific promoter, a fragment encoding PhaC fused to a peroxisomal targeting signal, and a poly adenylation signal can be constructed (FIG. 6C). The seed specific, peroxisomal PHA production construct can be transformed into *Arabidopsis* or oil seed crops such as *Brassica napus* as described in the previous examples.

Example 9

Production of Copolymers Comprised of Short and Medium Chain Length Monomer Units Co-polymers comprised of polyhydroxybutyrate and medium chain length monomer units can be produced in bacteria or plants by co-expressing pathways for 3-hydroxybutyryl CoA and medium chain length 3-hydroxyacyl CoA formation (FIG. 1). For short chain length monomer unit formation, a pathway consisting of a β-ketothiolase (phaA) and an acetoacetyl-CoA reductase (phaB) convert two units of acetyl CoA to R-3-hydroxybutyryl CoA (FIG. 1). For medium chain length monomer unit formation, a pathway consisting of a 3-hydroxy acyl ACP-thioesterase, such as PhaG, and an acyl CoA synthetase, such as AlkK, will convert medium chain length 3-hydroxyacyl ACPs from fatty acid biosynthesis to 3-hydroxy acyl CoAs (FIG. 1). Polymerization of the short and medium chain length monomer units into a copolymer is achieved with a PHA synthase possessing a broad substrate specificity, such as the synthase from *Pseudomonas* sp. A33 (Appl. Microbiol. Biotechnol. 1995, 42, 901-909), *Pseudomonas* sp. 61-3 (Kato, M., Bao, H. J., Kang, C. -K, Fukui, T., Doi, Y. Appl. Microbiol. Biotechnol. 1996, 45, 363-370), or *Thiocapsa pfennigii* (U.S. Pat. No. 6,011,144).

To produce copolymers comprised of PHB and medium chain length monomer units in the chloroplasts of leaves or plastids of seeds, transgenes encoding β-ketothiolase (phaA), acetoacetyl-CoA reductase (phaB), broad substrate specificity PHA synthase (phaC), 3-hydroxy acyl ACP thioesterase, and acyl CoA synthase are fused to a chloroplast or plastid targeting signal to direct the polypeptides to the chloroplasts or plastids for polymer production.

To produce copolymers comprised of PHB and medium chain length monomer units in the cytosol of leaves or seeds, the transgene encoding 3-hydroxy acyl ACP thioesterase is fused to a chloroplast or plastid targeting signal to direct the polypeptide to the chloroplasts or plastids. All other polypeptides, including β-ketothiolase, acetoacetyl-CoA reductase, broad substrate specificity PHA synthase, and acyl CoA synthetase are targeted to the cytosol resulting in polymer accumulation in the cytosol.

To produce copolymers comprised of PHB and medium chain length monomer units in the peroxisomes of leaves or seeds, the transgene encoding 3-hydroxy acyl ACP thioesterase is fused to a chloroplast or plastid targeting signal to direct the polypeptide to the chloroplasts or plastids. All other polypeptides, including β-ketothiolase, acetoacetyl-CoA reductase, broad substrate specificity PHA synthase, and acyl CoA synthase are fused to a peroxisomal targeting signal to direct the polypeptides to the peroxisomes for polymer production.

Those skilled in the art will recognize, or be able to ascertain using no more than routine experimentation, many equivalents to the specific embodiments of the invention described herein. Such equivalents are intended to be encompassed by the following claims.

We claim:

1. A genetically engineered organism selected from the group consisting of bacteria and plants expressing the enzymes for producing polyhydroxyalkanoate (PHA), further comprising a transgene encoding an enzyme having the catalytic activity of 3-hydroxyacyl-ACP thioesterase and one or more transgenes encoding enzymes having the catalytic activity of acyl-CoA synthetase or acyl CoA transferase so that medium chain length PHA accumulates through the fatty acid biosynthesis pathway.

2. The organism of claim 1 wherein the acyl-CoA synthetase is 3-hydroxyacyl-CoA synthetase.

3. The organism of claim 1 comprising a transgene alkK encoding an acyl-CoA synthetase.

4. The organism of claim 1 expressing a heterologous 3-hydroxyacyl-CoA synthetase activity.

5. The organism of claim 1 wherein one or more transgenes comprise a promoter to enhance expression in the genetically engineered organism.

6. The organism of claim 1 further comprising a transgene encoding an enzyme selected from the group consisting of medium chain length PHA synthase, and medium chain length 3-hydroxy fatty acid acyl CoA synthase, wherein the enzymes are expressed in a plant cell, plant tissue, plant organelle or whole plant.

7. The organism of claim 6 further expressing selectable marker genes, wherein the organism is a whole plant.

8. The organism of claim 1 further comprising a transgene encoding an enzyme selected from the group consisting of a PHA synthase that incorporates medium chain length hydroxy acids, and medium chain length 3-hydroxy fatty acid acyl CoA synthetase, wherein the organism is a bacteria.

9. The organism of claim 6 wherein the plant tissue or organelle is selected from the group consisting of seeds, leaf, plastids, and peroxisomes.

10. The organism of claim 8 wherein the bacteria is *E. coli* and PHA accumulates within the bacteria.

11. A method of engineering a PHA biosynthetic pathway in a transgenic organism selected from the group consisting of bacteria and plants expressing the enzymes for producing polyhydroxyalkanoate (PHA),
comprising providing the organism with one or more constructs comprising a transgene encoding an enzyme having the catalytic activity of 3-hydroxyacyl-ACP thioesterase and one or more transgenes encoding enzymes having the catalytic activity of acyl-CoA synthetase or acyl CoA transferase so that medium chain length PHA accumulates through the fatty acid biosynthesis pathway.

12. The method of claim 11 wherein the construct comprises a transgene encoding a 3-hydroxy acyl-CoA synthetase.

13. The method of claim 12 wherein the construct further comprises a transgene encoding a PHA synthase.

14. The method of claim 13 wherein the organism is a plant.

15. The method of claim 13 wherein the construct further comprises a transgene encoding an enzyme selected from the group consisting of medium chain length PHA synthase and medium chain length 3-hydroxy fatty acid acyl CoA synthase, wherein the enzymes are expressed in a plant cell, plant tissue, an organelle or whole plant.

16. The method of claim 13 wherein the construct further comprises a transgene encoding an enzyme selected from the group consisting of a PHA synthase that incorporates medium chain length hydroxy acids and medium chain length 3-hydroxy fatty acid acyl CoA synthetase, wherein the organism is a bacteria.

17. A method of making medium chain length PHA comprising growing a transgenic organism selected from the group consisting of bacteria and plants expressing the enzymes for producing polyhydroxyalkanoate (PHA), the organism expressing a transgene encoding an enzyme having the catalytic activity of 3-hydroxyacyl-ACP thioesterase and expressing one or more transgenes encoding enzymes having the catalytic activity of acyl-CoA synthetase or acyl CoA transferase, with substrates for fatty acid biosynthesis.

18. The method of claim 17 wherein the acyl-CoA synthetase is 3-hydroxyacyl-CoA synthetase.

19. The method of claim 17 wherein the organism further comprises a transgene encoding an enzyme selected from the group consisting of medium chain length PHA synthase, and medium chain length 3-hydroxy fatty acid acyl CoA synthase, wherein the enzymes are expressed in a plant cell, plant tissue, plant organelle or whole plant.

20. The method of claim 17 wherein the organism further comprises a transgene encoding an enzyme selected from the group consisting of a PHA synthase that incorporates medium chain length hydroxy acids and medium chain length 3-hydroxy fatty acid acyl CoA synthetase, wherein the organism is a bacteria.

21. The organism of claim 8 wherein the bacteria is *E. coli*, and wherein 3-hydroxy acids are secreted into the culture medium by the bacteria.

22. The method of claim 11, wherein the bacteria is *E. coli*, and wherein 3-hydroxy acids are secreted into the culture medium by the bacteria, further comprising collecting the 3-hydroxy acids from the medium.

* * * * *

SEQUENCE LISTING

<160> NUMBER OF SEQ ID NOS: 15

<210> SEQ ID NO 1
<211> LENGTH: 43
<212> TYPE: DNA
<213> ORGANISM: artificial sequence
<220> FEATURE:
<223> OTHER INFORMATION: primer phaGF-EcorI

<400> SEQUENCE: 1
ggaattcagg aggttttat gaggccagaa atcgctgtac ttg         43

<210> SEQ ID NO 2
<211> LENGTH: 37
<212> TYPE: DNA
<213> ORGANISM: artificial sequence
<220> FEATURE:
<223> OTHER INFORMATION: primer phaGR-KpnI

<400> SEQUENCE: 2 ggggtacccct cagatggcaa atgcatgctg cccctgc              37

<210> SEQ ID NO 3
<211> LENGTH: 49
<212> TYPE: DNA
<213> ORGANISM: artificial sequence
<220> FEATURE:
<223> OTHER INFORMATION: primer Posyn1-N

<400> SEQUENCE: 3
ccgaattcag gaggttttta ttatgagtaa caagaacaac gatgagctg  49

<210> SEQ ID NO 4
<211> LENGTH: 30
<212> TYPE: DNA
<213> ORGANISM: artificial sequence
<220> FEATURE:
<223> OTHER INFORMATION: primer Posyn1-nrSacII

<400> SEQUENCE: 4
ttggtcggag ccatggcttc ggtcatcagg                      30

<210> SEQ ID NO 5
<211> LENGTH: 40
<212> TYPE: DNA
<213> ORGANISM: artificial sequence
<220> FEATURE:
<223> OTHER INFORMATION: primer trc-PhaG.c

<400> SEQUENCE: 5
cccaagcttt ttgacaatta atcatccggc tcgtataatg           40

<210> SEQ ID NO 6
<211> LENGTH: 39
<212> TYPE: DNA
<213> ORGANISM: artificial sequence
<220> FEATURE:
<223> OTHER INFORMATION: primer trc-PhaG.r

<400> SEQUENCE: 6
cccaagcttt cagatggcaa atgcatgctg cccctgctg            39

<210> SEQ ID NO 7
<211> LENGTH: 45
<212> TYPE: DNA
<213> ORGANISM: artificial sequence
<220> FEATURE:
<223> OTHER INFORMATION: primer Posynrbs.c

<400> SEQUENCE: 7
ggaattcagg aggttttat gttaggtcag atgatgcgta atcag      45

<210> SEQ ID NO 8
<211> LENGTH: 35
<212> TYPE: DNA

<213> ORGANISM: artificial sequence
<220> FEATURE:
<223> OTHER INFORMATION: primerPosynrbs.r

<400> SEQUENCE: 8

| cgggatcctt attcacagac agaagaacta ctgcg | 35 |
|---|---|

<210> SEQ ID NO 9
<211> LENGTH: 911
<212> TYPE: DNA
<213> ORGANISM: artificial sequence
<220> FEATURE:
<223> OTHER INFORMATION: PhaG in the bacterial expression construct
    pMTX-PhaG

<400> SEQUENCE: 9

| gaattcagga ggtttttatg aggccagaaa tcgctgtact tgatatccaa ggtcagtatc | 60 |
|---|---|
| gggtttacac ggagttctat cgcgcggatg cggccgaaaa cacgatcatc ctgatcaacg | 120 |
| gctcgctggc caccacggcc tcgttcgccc agacggtacg taacctgcac ccacagttca | 180 |
| acgtggttct gttcgaccag ccgtattcag gcaagtccaa gccgcacaac cgtcaggaac | 240 |
| ggctgatcag caaggagacc gaggcgcata tcctccttga gctgatcgag cacttccagg | 300 |
| cagaccacgt gatgtctttt tcgtggggtg gcgcaagcac gctgctggcg ctggcgcacc | 360 |
| agccgcggta cgtgaagaag gcagtggtga gttcgttctc gccagtgatc aacgagccga | 420 |
| tgcgcgacta tctggaccgt ggctgccagt acctggccgc ctgcgaccgt tatcaggtcg | 480 |
| gcaacctggt caatgacacc atcggcaagc acttgccgtc gctgttcaaa cgcttcaact | 540 |
| accgccatgt gagcagcctg acagccacg agtacgcaca gatgcacttc cacatcaacc | 600 |
| aggtgctgga gcacgacctg aacgtgcgc tgcaaggcgc gcgcaatatc aacatcccgg | 660 |
| tgctgttcat caacggcgag gcgcgacgagt acaccacagt cgaggatgcg cggcagttca | 720 |
| gcaagcatgt gggcagaagc cagttcagcg tgatccgcga tgcgggccac ttcctggaca | 780 |
| tggagaacaa gaccgcctgc gagaacaccc gcaatgtcat gctgggcttc ctcaagccaa | 840 |
| ccgtgcgtga accccgccaa cgttaccaac ccgtgcagca ggggcagcat gcatttgcca | 900 |
| tctgaggtac c | 911 |

<210> SEQ ID NO 10
<211> LENGTH: 1715
<212> TYPE: DNA
<213> ORGANISM: artificial sequence
<220> FEATURE:
<223> OTHER INFORMATION: plasmid pTRCN-KPS1.2N. PhaC in the bacterial
    expression construct pKPS1.2N

<400> SEQUENCE: 10

| gaattcagga ggtttttatt atgagtaaca agaacaacga tgagctgcag cggcaggcct | 60 |
|---|---|
| cggaaaacac cctggggctg aacccggtca tcggtatccg ccgcaaagac ctgttgagct | 120 |
| cggcacgcac cgtgctgcgc caggccgtgc gccaaccgct gcacagcgcc aagcatgtgg | 180 |
| cccactttgg cctggagctg aagaacgtgc tgctgggcaa gtccagcctt gccccggaaa | 240 |
| gcgacgaccg tcgcttcaat gacccggcat ggagcaacaa cccactttac cgccgctacc | 300 |
| tgcaaaccta tctggcctgg cgcaaggagc tgcaggactg gatcggcaac agcgacctgt | 360 |
| cgccccagga catcagccgc ggccagttcg tcatcaacct gatgaccgaa gccatggctc | 420 |
| cgaccaaaca cctgtccaac ccggcagcag tcaaacgctt cttcgaaacc ggcggcaaga | 480 |
| gcctgctcga tggcctgtcc aacctggcca aggacctggt caacaacggt ggcatgccca | 540 |

-continued

```
gccaggtgaa catggacgcc ttcgaggtgg gcaagaacct gggcaccagt gaaggcgccg      600
tggtgtaccg caacgatgtg ctggagctga tccagtacaa ccccatcacc gagcaggtgc      660
atgcccgccc gctgctggtg gtgccgccgc agatcaacaa gttctacgta ttcgacctga      720
gcccggaaaa gagcctggca cgctactgcc tgcgctcgca gcagcagacc ttcatcatca      780
gctggcgcaa cccgaccaaa gcccagcgcg aatggggcct gtccacctac atcgacgcgc      840
tcaaggaggc ggtcgacgcg gtgctggcga ttaccggcag caaggacctg aacatgctcg      900
gtgcctgctc cggcggcatc acctgcacgg cattggtcgg ccactatgcc gccctcggcg      960
aaaacaaggt caatgccctg accctgctgg tcagcgtgct ggacaccacc atggacaacc     1020
aggtcgccct gttcgtcgac gagcagactt tggaggccgc caagcgccac tcctaccagg     1080
ccggtgtgct cgaaggcagc gagatggcca aggtgttcgc ctggatgcgc cccaacgacc     1140
tgatctggaa ctactgggtc aacaactacc tgctcggcaa cgagccgccg gtgttcgaca     1200
tcctgttctg gaacaacgac accacgcgcc tgccggccgc cttccacggc gacctgatcg     1260
aaatgttcaa gagcaacccg ctgacccgcc ggacgcgcct ggaggtttgc ggcactccga     1320
tcgacctgaa acaggtcaaa tgcgacatct acagccttgc cggcaccaac gaccacatca     1380
ccccgtggca gtcatgctac cgctcggcgc acctgttcgg cggcaagatc gagttcgtgc     1440
tgtccaacag cggccacatc cagagcatcc tcaacccgcc aggcaacccc aaggcgcgct     1500
tcatgaccgg tgccgatcgc ccgggtgacc cggtggcctg caggaaaaac gccaccaagc     1560
atgccgactc ctggtggctg cactggcaaa gctggctggg cgagcgtgcc ggcgagctgg     1620
aaaaggcgcc gacccgcctg gcaaccgtgc ctatgccgc tggcgaggca tccccgggca     1680
cctacgttca cgagcgttga gctgcagcca agctt                                1715
```

<210> SEQ ID NO 11
<211> LENGTH: 2703
<212> TYPE: DNA
<213> ORGANISM: artificial sequence
<220> FEATURE:
<223> OTHER INFORMATION: plasmid pSU-PhaCp.o.trc.PhaG

<400> SEQUENCE: 11

```
gaattcagga ggttttttatt atgagtaaca agaacaacga tgagctgcag cggcaggcct       60
cggaaaacac cctggggctg aacccggtca tcggtatccg ccgcaaagac ctgttgagct      120
cggcacgcac cgtgctgcgc caggccgtgc gccaaccgct gcacagcgcc aagcatgtgg      180
cccactttgg cctggagctg aagaacgtgc tgctgggcaa gtccagcctt gccccggaaa      240
gcgacgaccg tcgcttcaat gacccggcat ggagcaacaa cccactttac cgccgctacc      300
tgcaaaccta tctggcctgg cgcaaggagc tgcaggactg gatcggcaac agcgacctgt      360
cgccccagga catcagccgc ggccagttcg tcatcaacct gatgaccgaa gccatggctc      420 gaccaacac cctgtccaac ccggcagcag tcaaacgctt cttcgaaacc ggcggcaaga      480
gcctgctcga tggcctgtcc aacctggcca aggacctggt caacaacggt ggcatgccca      540
gccaggtgaa catggacgcc ttcgaggtgg gcaagaacct gggcaccagt gaaggcgccg      600
tggtgtaccg caacgatgtg ctggagctga tccagtacaa gcccatcacc gagcaggtgc      660
atgcccgccc gctgctggtg gtgccgccgc agatcaacaa gttctacgta ttcgacctga      720
gcccggaaaa gagcctggca cgctactgcc tgcgctcgca gcagcagacc ttcatcatca      780
gctggcgcaa cccgaccaaa gcccagcgcg aatggggcct gtccacctac atcgacgcgc      840
```

```
tcaaggaggc ggtcgacgcg gtgctggcga ttaccggcag caaggacctg aacatgctcg      900
gtgcctgctc cggcggcatc acctgcacgg cattggtcgg ccactatgcc gccctcggcg      960
aaaacaaggt caatgccctg accctgctgg tcagcgtgct ggacaccacc atggacaacc     1020
aggtcgccct gttcgtcgac gagcagactt tggaggccgc caagcgccac tcctaccagg     1080
ccggtgtgct cgaaggcagc gagatggcca aggtgttcgc ctggatgcgc ccaacgacc      1140 tgatctggaa ctactgggtc aacaactacc tgctcggcaa cgagccgccg gtgttcgaca     1200
tcctgttctg gaacaacgac accacgcgcc tgccggccgc cttccacggc gacctgatcg     1260
aaatgttcaa gagcaacccg ctgacccgcc ggacgccct ggaggtttgc ggcactccga      1320
tcgacctgaa acaggtcaaa tgcgacatct acagccttgc cggcaccaac gaccacatca     1380
ccccgtggca gtcatgctac cgctcggcgc acctgttcgg cggcaagatc gagttcgtgc     1440
tgtccaacag cggccacatc cagagcatcc tcaacccgcc aggcaacccc aaggcgcgct     1500
tcatgaccgg tgccgatcgc ccgggtgacc cggtggcctg caggaaaac gccaccaagc      1560 atgccgactc ctggtggctg cactggcaaa gctggctggg cgagcgtgcc ggcgagctgg     1620
aaaaggcgcc gacccgcctg gcaaccgtg cctatgccgc tggcgaggca tccccgggca     1680
cctacgttca cgagcgttga gctgcagcca agcttttgac aattaatcat ccggctcgta     1740
taatgtgtgg aattgtgagc ggataacaat ttcacacagg aaacagacca tggaattcag     1800
gaggttttta tgaggccaga aatcgctgta cttgatatcc aaggtcagta tcgggtttac     1860
acggagttct atcgcgcgga tgcggccgaa aacacgatca tcctgatcaa cggctcgctg     1920
gccaccacgg cctcgttcgc ccagacggta cgtaacctgc acccacagtt caacgtggtt     1980
ctgttcgacc agccgtattc aggcaagtcc aagccgcaca accgtcagga acggctgatc     2040
agcaaggaga ccgaggcgca tatcctcctt gagctgatcg agcacttcca ggcagaccac     2100
gtgatgtctt tttcgtgggg tggcgcaagc acgctgctgg cgctggcgca ccagccgcgg     2160
tacgtgaaga aggcagtggt gagttcgttc tcgccagtga tcaacgagcc gatgcgcgac     2220
tatctggacc gtggctgcca gtacctggcc gcctgcgacc gttatcaggt cggcaacctg     2280
gtcaatgaca ccatcggcaa gcacttgccg tcgctgttca aacgcttcaa ctaccgccat     2340
gtgagcagcc tggacagcca cgagtacgca cagatgcact ccacatcaa ccaggtgctg     2400 gagcacgacc tggaacgtgc gctgcaaggc gcgcgcaata tcaacatccc ggtgctgttc     2460
atcaacggcg agcgcgacga gtacaccaca gtcgaggatg cgcggcagtt cagcaagcat     2520
gtgggcagaa gccagttcag cgtgatccgc gatgcgggcc acttcctgga catggagaac     2580
aagaccgcct gcgagaacac ccgcaatgtc atgctgggct tcctcaagcc aaccgtgcgt     2640
gaaccccgca acgttacca acccgtgcag caggggcagc atgcatttgc catctgaaag     2700
ctt                                                                    2703
```

<210> SEQ ID NO 12
<211> LENGTH: 1664
<212> TYPE: DNA
<213> ORGANISM: artificial sequence
<220> FEATURE:
<223> OTHER INFORMATION: alkK in the bacterial expression construct pTRCNalkK

<400> SEQUENCE: 12

```
gaattcagga ggttttatg ttaggtcaga tgatgcgtaa tcagttggtc attggttcgc       60
ttgttgagca tgctgcacga tatcatggtg cgagagaggt ggtttcagtc gaaacctctg      120
```

-continued

| | |
|---|---|
| gagaagtaac aagaagttgt tggaaagaag tggagcttcg tgctcgtaag ctcgcttctg | 180 |
| cattgggcaa gatgggtctt acgcctagtg atcgttgtgc aacgattgca tggaacaata | 240 |
| ttcgtcatct tgaggtttac tacgctgtct ctggcgcagg aatggtatgc catacaatca | 300 |
| atccgaggct tttcattgag cagatcacat atgtgataaa ccatgcggag ataaggtag | 360 |
| tatttcttga tgatacgttc ttgccaatca ttgctgagat cgcggttcg ttaccaaaag | 420 |
| tcaaggcgtt tgtcttgatg gctcataata attcaaatgc atctgctcaa atgccaggat | 480 |
| tgattgcata cgaggatcta attggtcagg gtgatgataa ctatatatgg cctgatgtag | 540 |
| atgaaaatga ggcgtctagt ctatgttaca catcaggtac tacgggcaac ccgaaggtg | 600 |
| tactttattc acaccgctcg acagttttgc attcaatgac caccgcaatg ccagacacac | 660 |
| taaatttgtc tgcgcgagat accatttgc ccgtagttcc aatgtttcat gtaaatgcat | 720 |
| ggggactcc atattccgct gcaatggttg gtgcgaagct agttcttcct ggtccggctc | 780 |
| ttgatggcgc tagtttatcg aagttgattg ctagcgaagg agttagcatt gctcttgggg | 840 |
| tgccggttgt ttggcagggg ttgttagcgg cacaagccgg taatggttct aaaagccaaa | 900 |
| gcctcacgcg ggttgttgta ggaggttcgg cctgtcctgc gtctatgatt agagaatta | 960 |
| acgatatata tggtgttgaa gttattcatg cttggggtat gactgagctt tcgccatttg | 1020 |
| gcacggcaaa cactccactc gcgcaccacg tagatttatc tccagatgaa aagctttcac | 1080 |
| tgcgcaaaag ccaagggcgc ccgccttacg gtgtcgagtt aaaaatcgtt aatgatgagg | 1140 |
| ggattagact acctgaagat ggtcgaagta aaggcaacct aatggcgcgt gggcactggg | 1200 |
| ttattaaaga ttactttcat agcgatcctg gttcgacact ctcagatggt tggttttcaa | 1260 |
| ctggagacgt ggctaccata gattcggacg gtttcatgac aatctgtgat cgtgcaaagg | 1320 |
| acattataaa gtctggcggt gagtggatca gtacggtaga gctggagagt attgcgattg | 1380 |
| cgcaccctca tattgttgat gctgctgtta tagctgcaag gcacgaaaaa tgggacgagc | 1440 |
| gacctctcct catcgcagtt aaatcccta attcggaatt aacaagtggt gaggtatgta | 1500 |
| attatttcgc agataaggtg gctagatggc aaattccaga tgccgctatc tttgttgaag | 1560 |
| aactgccacg caatggtact ggcaagattt tgaagaatcg tttgcgcgag aaatatggtg | 1620 |
| atattttatt gcgcagtagt tcttctgtct gtgaataagg atcc | 1664 |

<210> SEQ ID NO 13
<211> LENGTH: 1653
<212> TYPE: DNA
<213> ORGANISM: artificial sequence
<220> FEATURE:
<223> OTHER INFORMATION: alkK in the plant expression construct pUC-C4PPDK.TS.AlkK

<400> SEQUENCE: 13

| | |
|---|---|
| tctagaatgt taggtcagat gatgcgtaat cagttggtca ttggttcgct tgttgagcat | 60 |
| gctgcacgat atcatggtgc gagagaggtg gtttcagtcg aaacctctgg agaagtaaca | 120 |
| agaagttgtt ggaaagaagt ggagcttcgt gctcgtaagc tcgcttctgc attgggcaag | 180 |
| atgggtctta cgcctagtga tcgttgtgca acgattgcat ggaacaatat tcgtcatctt | 240 |
| gaggtttact acgctgtctc tggcgcagga atggtatgcc atacaatcaa tccgaggctt | 300 |
| ttcattgagc agatcacata tgtgataaac catgcggagg ataaggtagt atttcttgat | 360 |
| gatacgttct tgccaatcat tgctgagatt cgcggttcgt taccaaaagt caaggcgttt | 420 |
| gtcttgatgg ctcataataa ttcaaatgca tctgctcaaa tgccaggatt gattgcatac | 480 |

```
gaggatctaa ttggtcaggg tgatgataac tatatatggc ctgatgtaga tgaaaatgag      540
gcgtctagtc tatgttacac atcaggtact acgggcaacc cgaagggtgt actttattca      600
caccgctcga cagttttgca ttcaatgacc accgcaatgc cagacacact aaatttgtct      660
gcgcgagata ccattttgcc cgtagttcca atgtttcatg taaatgcatg ggggactcca      720
tattccgctg caatggttgg tgcgaagcta gttcttcctg gtccggctct tgatggcgct      780
agtttatcga agttgattgc tagcgaagga gttagcattg ctcttggggt gccggttgtt      840
tggcaggggt tgttagcggc acaagccggt aatggttcta aaagccaaag cctcacgcgg      900
gttgttgtag gaggttcggc ctgtcctgcg tctatgatta gagaatttaa cgatatatat      960
ggtgttgaag ttattcatgc ttggggtatg actgagcttt cgccatttgg cacggcaaac     1020
actccactcg cgcaccacgt agatttatct ccagatgaaa agctttcact gcgcaaaagc     1080
caagggcgcc cgccttacgg tgtcgagtta aaaatcgtta atgatgaggg gattagacta     1140
cctgaagatg gtcgaagtaa aggcaaccta atggcgcgtg ggcactgggt tattaaagat     1200
tactttcata gcgatcctgg ttcgacactc tcagatggtt ggttttcaac tggagacgtg     1260
gctaccatag attcggacgg tttcatgaca atctgtgatc gtgcaaagga cattataaag     1320
tctggcggtg agtggatcag tacggtagag ctggagagta ttgcgattgc gcaccctcat     1380
attgttgatg ctgctgttat agctgcaagg cacgaaaaat gggacgagcg acctctcctc     1440
atcgcagtta aatcccctaa ttcggaatta acaagtggtg aggtatgtaa ttatttcgca     1500
gataaggtgg ctagatggca aattccagat gccgctatct ttgttgaaga actgccacgc     1560
aatggtactg gcaagatttt gaagaatcgt ttgcgcgaga aatatggtga tattttattg     1620
cgcagtagtt cttctgtctg tgaataaggt acc                                  1653

<210> SEQ ID NO 14
<211> LENGTH: 6
<212> TYPE: DNA
<213> ORGANISM: artificial sequence
<220> FEATURE:
<223> OTHER INFORMATION: XbaI restriction site

<400> SEQUENCE: 14 tctaga                                                                    6

<210> SEQ ID NO 15
<211> LENGTH: 6
<212> TYPE: DNA
<213> ORGANISM: artificial sequence
<220> FEATURE:
<223> OTHER INFORMATION: KpnI restriction site

<400> SEQUENCE: 15 ggtacc                                                                    6
```